US011031093B2

(12) United States Patent
Lakatos et al.

(10) Patent No.: US 11,031,093 B2
(45) Date of Patent: Jun. 8, 2021

(54) SYSTEMS AND METHODS FOR IDENTIFYING THERMODYNAMICALLY RELEVANT POLYMER CONFORMATIONS

(71) Applicant: ZYMEWORKS INC., Vancouver (CA)

(72) Inventors: Gregory Lakatos, Vancouver (CA); Surjit Bhimarao Dixit, Richmond (CA)

(73) Assignee: ZYMEWORKS INC., Vancouver (CA)

(*) Notice: Subject to any disclaimer, the term of this patent is extended or adjusted under 35 U.S.C. 154(b) by 89 days.

(21) Appl. No.: 14/409,419

(22) PCT Filed: Jun. 21, 2013

(86) PCT No.: PCT/CA2013/050489
§ 371 (c)(1),
(2) Date: Dec. 18, 2014

(87) PCT Pub. No.: WO2013/188984
PCT Pub. Date: Dec. 27, 2013

(65) Prior Publication Data
US 2015/0142326 A1    May 21, 2015

Related U.S. Application Data

(60) Provisional application No. 61/662,549, filed on Jun. 21, 2012.

(51) Int. Cl.
| | | |
|---|---|---|
| *G16B 15/00* | (2019.01) | |
| *G01N 33/68* | (2006.01) | |
| *C07K 1/00* | (2006.01) | |
| *G16C 20/30* | (2019.01) | |
| *G16C 20/70* | (2019.01) | |

(52) U.S. Cl.
CPC .............. *G16B 15/00* (2019.02); *C07K 1/00* (2013.01); *G01N 33/68* (2013.01); *G16C 20/30* (2019.02); *C07K 2299/00* (2013.01); *G16C 20/70* (2019.02)

(58) Field of Classification Search
None
See application file for complete search history.

(56) References Cited

U.S. PATENT DOCUMENTS

| 7,751,987 B1 | 7/2010 | Becker et al. |
| 2003/0215877 A1 | 11/2003 | Love et al. |
| 2006/0040322 A1 | 2/2006 | Archetti et al. |
| 2008/0033659 A1 | 2/2008 | Zelma et al. |
| 2011/0053261 A1 | 3/2011 | Lario et al. |

FOREIGN PATENT DOCUMENTS

WO    WO 2003/072596 A2    9/2003

OTHER PUBLICATIONS

Baker & Hubbard, 1984, "Hydrogen Bonding in Globular Proteins," Prog. Biophy. Mol. Biol., 44, 97-179.
Boczko, 1995, "First-Principles Calculation of the Folding Free Energy of a Three-Helix Bundle Protein," Science 21 393.
Cornell et al., 1995, "A Second Generation Force Field for the Simulation of Proteins," Nucleic Acids, and Organic Molecules, J. Am. Chem. Soc. 117: 5179-5197.
Desmet et al., 1992, "The dead-end elimination theorem and its use in protein side-chain position", Nature 356: 539-542.
Dunbrack and Karplus, 1993, "Backbone-dependent rotamer library for proteins. Application to side chain prediction," J. Mol. Biol. 230: 543-574.
Eidhammer et al., 2000, Structure Comparison and Structure Patterns, Journal of Computational Biology, vol. 7, No. 5: 685-716.
Georgiev et al., 2007, "Algorithm for backrub motions in protein design," Comp. Chem. 29 1527.
Glick et al., 2002, "A stochastic algorithm for global optimization and for best populations: A test case of side chains in proteins," PNAS 99, 703.
Goldstein, 1994, "Efficient rotamer elimination applied to protein side chains and related spin glasses", Biophys. J. 66: 1335-1340.
Kirkpatrick et al., 1983, "Optimization by Simulated Annealing," Science 220, 4598.
Kloppmann et al., 2007, "An Extended Dead-End Elimination Algorithm to Determine Gap-Free Lists of Low Energy States," J. Comp Chem. 28, 2325.
Lasters et al., 1995, "Enhanced dead-end elimination in the search for the global minimum energy conformation of a collection of protein side chains", Protein Eng. 8: 815-822.
Leach and Lemon, 1998, "Exploring the Conformational Space of Protein Side Chains Using Dead-End Elimination and the A* Algorithm", Proteins: Structure, Function, and Genetics 33: 227-239.
Lovell et al., 2000, "The Penultimate Rotamer Library," Proteins: Structure Function and Genetics 40: 389-408.
Ponder and Case, 2003, "Force fields for protein simulations," Adv. Prot. Chem. 66, p. 27.

(Continued)

*Primary Examiner* — Michael L Borin
(74) *Attorney, Agent, or Firm* — Morgan, Lewis & Bockius LLP; Brett Lovejoy

(57) ABSTRACT

Systems, methods and non-transitory computer readable media identify favored polymer conformations. One or more residues are identified and may be replaced in the polymer, or the original primary sequence of the polymer may be retained. The conformations of residues in a subset of residues in a region of the identified one or more residues are altered. This conformational adjustment is repeated for other subsets of residues in the region of the identified one or more residues, and for other conformations, thereby deriving a plurality of polymer structures. A set of clusters is generated for each residue of the polymer using the conformationally adjusted structures, thereby creating sets of clusters. Structures in the plurality of structures are grouped into subgroups when the structures fall into the same clusters across a threshold number of the sets of clusters. One or more physical properties are determined for structures in subgroups, thereby identifying one or more thermodynamically relevant polymer conformations for the polymer.

30 Claims, 7 Drawing Sheets

(56) References Cited

OTHER PUBLICATIONS

Shao et al., 2007, "Clustering Molecular Dynamics Trajectories: 1. Characterizing the Performance of Different Clustering Algorithms," J. Chem. Theory Comput. 3, 2312.
Shapovalov and Dunbrack, 2011, "A smoothed backbone-dependent rotamer library for proteins derived from adaptive kernel density estimates and regressions," Structure 19, 844-858.
Xiang and Honig, 2001, "Extending the Accuracy Limits of Prediction for Side-chain Conformations," Journal of Molecular Biology 311, p. 421.

| | |
|---|---|
| Cluster results | /– 72 |
| Set of clusters for mutated polymer residue 1 side chain | /– 202-1 |
| Cluster for side chain conformation 1 of residue 1 side chain | /– 204-1-1 |
| Identity of mutated polymer structure having side chain conformation 1 of residue 1 side chain | /– 206-1-1-1 |
| ⋮ | |
| Identity of mutated polymer structure having side chain conformation 1 of residue 1 side chain | /– 206-1-1-R |
| Cluster for side chain conformation 2 of residue 1 side chain | /– 204-1-2 |
| Identity of mutated polymer structure having side chain conformation 2 of residue 1 side chain | /– 206-1-2-1 |
| ⋮ | |
| Identity of mutated polymer structure having side chain conformation 2 of residue 1 side chain | /– 206-1-2-S |
| ⋮ | |
| Cluster for side chain conformation Q of residue 1 side chain | /– 204-1-Q |
| Identity of mutated polymer structure having side chain conformation Q of residue 1 side chain | /– 206-1-Q-1 |
| ⋮ | |
| Identity of mutated polymer structure having side chain conformation Q of residue 1 side chain | /– 206-1-Q-T |
| Set of clusters for mutated polymer residue 1 main chain | /– 208-1 |
| Cluster for main chain conformation 1 of residue 1 main chain | /– 210-1-1 |
| Identity of mutated polymer structure having main chain conformation 1 of residue 1 main chain 1 | /– 212-1-1-1 |
| ⋮ | |
| Identity of mutated polymer structure having main chain conformation 1 of residue 1 main chain | /– 212-1-1-Z |
| ⋮ | |
| Cluster for main chain conformation P of residue 1 main chain | /– 210-1-P |
| Set of clusters for mutated polymer residue 2 side chain | /– 202-2 |
| Clusters for side chain conformations of residue 2 side chain | /– 204-2-V |
| Set of clusters for mutated polymer residue 2 main chain | /– 208-2 |
| Clusters for main chain conformations of residue 2 main chain | /– 210-2-W |
| ⋮ | |
| Set of clusters for mutated polymer residue N side chain | /– 202-N |
| Clusters for side chain conformations of residue N side chain | /– 204-N-(1-X) |
| Set of clusters for mutated polymer residue N main chain | /– 208-N |
| Clusters for main chain conformations of residue N main chain | /– 210-N-(1-Y) |

Fig. 2

| Subgroup results | 76 |
|---|---|
| Subgroup 1 - mutated polymer structures having side chain and main chain conformations falling into the same respective clusters 204 / 210 across the plurality of sets of clusters 202 / 208 | 302-1 |
|     Identity of mutated polymer structure | 304-1-1 |
|     ⋮ | |
|     Identity of mutated polymer structure | 304-1-Q |
| Physical property of the mutated polymer structures of subgroup 1 | 306-1 |
| Subgroup 2 - mutated polymer structures having side chain and main chain conformations falling into the same respective clusters 204 / 210 across the plurality of sets of clusters 202 / 208 | 302-2 |
|     Identity of mutated polymer structure | 304-2-1 |
|     ⋮ | |
|     Identity of mutated polymer structure | 304-2-R |
| Physical property of the mutated polymer structures of subgroup 2 | 306-2 |
| ⋮ | |
| Subgroup M - mutated polymer structures having side chain and main chain conformations falling into the same respective clusters 204 / 210 across the plurality of sets of clusters 202 / 208 | 302-M |
|     Identity of mutated polymer structure | 304-M-1 |
|     ⋮ | |
|     Identity of mutated polymer structure | 304-M-T |
| Physical property of the mutated polymer structures of subgroup M | 306-M |

Fig. 3

|  | Mutated polymer structure 56-1 | Mutated polymer structure 56-2 | ... | Mutated polymer structure 56-M |
|---|---|---|---|---|
| Cluster 204 identity for side chain of residue 1 of the sequence of mutated polymer 55 | Cluster 204-1-1 of the set of clusters 202-1 | Cluster 204-1-5 of the set of clusters 202-1 |  | Cluster 204-1-1 of the set of clusters 202-1 |
| Cluster 210 identity for main chain of residue 1 of the sequence of mutated polymer 55 | Cluster 210-1-7 of the set of clusters 208-1 | Cluster 210-1-3 of the set of clusters 208-1 |  | Cluster 210-1-7 of the set of clusters 208-1 |
| Cluster 204 identity for side chain of residue 2 of the sequence of mutated polymer 55 | Cluster 204-2-5 of the set of clusters 202-2 | Cluster 204-2-2 of the set of clusters 202-2 |  | Cluster 204-2-5 of the set of clusters 202-2 |
| Cluster 210 identity for side chain of residue 2 of the sequence of mutated polymer 55 | Cluster 210-2-12 of the set of clusters 208-2 | Cluster 210-2-11 of the set of clusters 208-2 |  | Cluster 210-2-12 of the set of clusters 208-2 |
| ⋮ | ⋮ | ⋮ | ⋮ | ⋮ |
| Cluster 204 identity for side chain of residue N of the sequence of mutated polymer 55 | Cluster 204-N-1 of the set of clusters 202-N | Cluster 204-N-102 of the set of clusters 202-N |  | Cluster 204-N-1 of the set of clusters 202-N |
| Cluster 210 identity for main chain of residue N of the sequence of mutated polymer 55 | Cluster 210-N-4 of the set of clusters 208-N | Cluster 210-N-6 of the set of clusters 208-N |  | Cluster 210-N-4 of the set of clusters 208-N |

Fig. 6

SYSTEMS AND METHODS FOR IDENTIFYING THERMODYNAMICALLY RELEVANT POLYMER CONFORMATIONS

CROSS-REFERENCE TO RELATED APPLICATION

This application claims priority under 35 U.S.C. § 116(e) the benefit of U.S. Application No. 61/662,549, filed Jun. 21, 2012, which is hereby incorporated by reference herein in its entirety.

TECHNICAL FIELD

The disclosed embodiments relate generally to systems and methods for identifying thermodynamically relevant polymer conformations. The disclosed embodiments have wide application in efforts in understanding the physical properties of polymers and, based on this understanding, improving the physical properties of polymers.

BACKGROUND

Knowledge of the ensemble of thermodynamically relevant polymer structures for a given residue sequence is desired in order to advance polymer engineering. For instance, knowledge of the ensemble of thermodynamically relevant protein structures for a given primary sequence facilitates the identification of those substitutions that will lead to a protein having more desirable physical characteristics.

Protein engineering frequently involves investigating the properties of a known wild-type sequence, making mutations in a protein of known sequence and structure, and evaluating the effects of these mutations on properties such as protein fold stability, or protein binding. An understanding of the thermodynamically relevant structural configurations of the wild-type and mutated proteins is beneficial when evaluating the effects of such mutations.

To illustrate, consider the case in which an antibody is optimized with respect to a physical property of the antibody, such as an antigen binding coefficient, antigen selectivity, or thermostability. Towards this goal, a protein engineer may study the thermodynamically relevant structural configurations of the residues of the wild-type antibody, and on the basis of these results, elect to mutate one or more residues of the antibody thereby causing the protein sequence to change. This causes the geometry of the residues relative to each other to change. Knowledge of the thermodynamically relevant geometric configurations of the antibody residues after mutation, and how these geometries differ from those exhibited by the wild-type, aids in understanding the effects of the mutations on antibody properties.

One approach to the problem assumes that knowledge of the thermodynamic ground state of the mutated polymer (e.g., protein, nucleic acid) is sufficient to evaluate the effects of the mutation. Unfortunately, this approach is limited because low free energy states distinct from the ground state are common, and can profoundly affect polymer behavior.

An alternative approach to evaluating the effects of mutations is the use of complex sampling schemes, such as molecular dynamics, that can be used to generate an ensemble of alternate conformations, and approximate thermodynamic properties can be computed from this ensemble. While useful in principle, the thermodynamic averages produced by this approach are often inaccurate, and the sheer size of the generated ensembles make detailed structural analysis challenging.

Specific approaches have been published. For example, Leach and Lemon, 1998, Prot: Struct, Function, Genetics 33, 227 describe a variant of the dead end elimination algorithm that is capable of identifying the enthalpic ground state of side chains in rotamer space, and providing alternate low energy conformations. The partition function for the entire optimized space is computed. However, no clustering is performed, local partition functions for multiple structural states are not identified, and the paper's method is not extensible to continuum sampling schemes.

Glick et al., 2002, PNAS 99, 703 describe a rotameric search methodology capable of identifying the enthalpic ground state, as well as alternate low energy states. Partition functions are not explicitly computed. However, the possibility of estimating the total partition function for the entire optimized region is discussed. However, no clustering is performed, local partition functions for multiple structural states are not identified, and the paper's method is not extensible to continuum sampling schemes.

Kloppmann et al., 2007, J. Comp Chem. 28, 2325, propose an extension of the dead end elimination method for optimization in rotameric space is that can provide a gap-free list of low energy states. The generated ensemble is used to compute a partition function for the entire optimized region. Clustering is not used, and the method cannot be applied to results from continuum sampling methods.

Georgiev et al., 2007 Comp. Chem. 29 1527, provide a hybrid dead-end elimination/coordinate minimization algorithm that works both in rotamer space and in continuous degrees of freedom. An ensemble of low energy states is produced by the algorithm, and a partition function for the optimized region is computed. No clustering in rotamer or continuous space is performed, and the approach described in this reference is not applicable to analysis of results from conformational searches performed exclusively over continuous degrees of freedom.

Boczko, 1995, Science 21 393, examine the states along the unfolding pathway of a small protein, where a state was defined by clustering molecular dynamics trajectories. However, the clustering is performed on a large scale, across many degrees of freedom, rather than individually on each side chain and backbone. Moreover, the entire motivation for performing clustering in this reference is to define protein states in order to evaluate the folding pathway of a protein, rather than to define alternate structures that make significant contributions to the thermodynamic properties of a mutated, but folded, protein.

Shao et al., 2007, J. Chem. Theory Comput. 3, 2312 describe several clustering algorithms appropriate for the task of identifying conformational states, and apply these methods to the analysis of molecular dynamics trajectories. However, the clustering is applied to sets of coordinates that cover multiple structural elements, rather than being applied on a per-structural unit basis (e.g. per side chain and per mobile backbone region). Furthermore, there is no concept of computing local partition functions, or identifying alternate thermodynamically relevant configurations for the purpose of evaluating the effects of a mutation on the properties of a protein in the reference.

Given the above background, what is needed in the art are systems and methods that overcome the limitations of these two common approaches, and a procedure capable of identifying thermodynamically relevant configurations of a polymer or polymer region, in a manner amenable to manual or automated analysis by a polymer engineer.

SUMMARY

The present disclosure describes systems and methods for identifying the thermodynamically relevant configurations of a polymer or polymer region. The systems and methods combine configurational sampling and structural clustering algorithms in novel ways to identify sets of polymer configurations that are mutually distinct, and have free energies close to the thermodynamic ground state. The systems and methods are general, and are capable of analyzing both residue side chain and residue backbone structural variability, and doing so in a coupled fashion when desired.

One aspect provides a method of identifying a thermodynamically relevant conformation for a polymer comprising a plurality of atoms. The method comprises, at a computer system having one or more processors and memory storing one or more programs to be executed by the one of more processors, obtaining an initial set of three-dimensional coordinates $\{x_1, \ldots, x_N\}$ for the polymer. Each respective $x_i$ in $\{x_1, \ldots, x_N\}$ is a three dimensional coordinate for an atom in the plurality of atoms. In some embodiments, the initial set of three-dimensional coordinates $\{x_1, \ldots, x_N\}$ for the polymer are obtained by x-ray crystallography, nuclear magnetic resonance, electron microscopy, or computer modeling.

In silico, one or more residues of the polymer are identified and are optionally replaced with different residues. If no residue replacement occurs, the method proceeds using the wild-type residues. Subsequently at least one region of the polymer is defined, and this region may or may not contain the identified residues. Next, the conformation is altered, with respect to the initial set of three-dimensional coordinates $\{x_1, \ldots, x_N\}$ for the polymer, in each respective subset of residues in the region of the polymer in a plurality of subsets of residues in the region of the polymer, of each residue in the respective subset of residues. The coordinates that may be altered include the coordinates of the main chain and the side chains of the subset of residues in the region of the polymer. This alteration of coordinates results in a plurality of structures of the region of the polymer. Each respective subset of residues in the plurality of subsets of residues in the region of the polymer is selected from among all the residues in the region of the polymer using a deterministic, randomized or pseudo-randomized algorithm.

Next, in some embodiments, a set of clusters is generated for each respective residue in the region of the polymer using the plurality of structures, thereby creating a plurality of sets of clusters. Each set of clusters in the plurality of sets of clusters is for a side chain or a main chain of a different residue in the region of the polymer. Alternatively, contiguous main chain segments may be clustered as individual units. In such embodiments, each set of clusters in the plurality of sets of clusters is either for (i) a side chain of a different residue in the region of the polymer or (ii) for a contiguous set of main chain elements. A first structure in the plurality of structures is placed in a first cluster in a first set of clusters in the plurality of sets of clusters and a second structure in the plurality of structures is placed in a second cluster in the first set of clusters when a structural characteristic associated with the coordinates of the side chain or the main chain of the residue, represented by the first set of clusters, in the first structure deviates from a structural characteristic associated with the coordinates of the side chain or the main chain of the residue in the second structure by a threshold amount.

The plurality of sets of clusters is used to group the plurality of structures into a plurality of subgroups. For this grouping, the condition is imposed that each structure in a subgroup in the plurality of subgroups falls into the same cluster in a threshold number of the sets of clusters in the plurality of sets of clusters. In some embodiments, the threshold number of the sets of clusters is all the sets of clusters in the plurality of sets of clusters. In some embodiments, the threshold number of the sets of clusters is all but one of the sets of clusters in the plurality of sets of clusters. In some embodiments, the threshold number of the sets of clusters is ninety percent of the sets of clusters in the plurality of sets of clusters.

Next, one or more properties of a plurality of structures in a subgroup in the plurality of subgroups is determined. In some embodiments, a property in the one or more properties of the plurality of structures in the subgroup in the plurality of subgroups is a mean distance between a first point in the plurality of structures and a second point in the plurality of structures. In some embodiments, a property in the one or more properties of the plurality of structures in the subgroup in the plurality of subgroups is a mean distance between a first point in the plurality of structures and a second point in a molecule that binds to the polymer or is bound by the polymer. In some embodiments, a property in the one or more properties of the plurality of structures in the subgroup in the plurality of subgroups is a mean energy of the plurality of structures. In some embodiments, a property in the one or more properties of the plurality of structures in the subgroup in the plurality of subgroups is the minimum energy of the plurality of structures. More than one property may be considered at the same time, and a function of the properties considered can be used to identify those clusters that represent thermodynamically relevant geometries of the polymer.

In some embodiments, each residue in a plurality of residues in the region of the polymer is replaced with a different residue. In some embodiments, two residues, three residues, four residues, five residues, or more than six residues in the region of the polymer are replaced with different residues. In some embodiments, no residue replacement occurs, and the wild-type sequence of the polymer is used.

In some embodiments, the region of the polymer consists of the atoms in the plurality of atoms that are within a distance threshold of the residue of the polymer. In some embodiments, the distance threshold is "X" Angstroms, where "X" is any value between 5 and 50 (e.g., 5, 10, 15, 20, 25, 30, 35, 40, 45, 50, etc.).

In some embodiments, the conformations are altered, for each respective subset of residues in the region of the polymer in the plurality of independent overlapping subsets of residues in the region of the polymer, of each residue in the respective subset of residues (b) by: (i) setting a value t to an initial value and defining an initial structure to be the initial set of three-dimensional coordinates $\{x_1, \ldots, x_N\}$ for the polymer, (ii) altering a conformation of each residue in a subset of residues in the polymer from that found in the initial structure thereby deriving a structure in the plurality of structures, (iii) accepting the structure derived in (ii) as the initial structure when a score from a scoring function of the structure derived in (ii) is less than an score from the scoring function for the initial structure, (iv) accepting, with a probability $P(\Delta E)$, the structure derived in (ii) as the initial structure when the score of the structure derived in (ii) is greater than the score of the initial structure, where P(ΔE) is a probability function that is dependent upon (1) a difference in score between the initial structure and the structure derived in (ii) and (2) the value t, (v) decreasing the value t by an amount, and (vi) executing (ii) through (v) until a first occurrence of an exit condition, thereby deriving the plurality of structures of the region of the polymer. In some embodiments, $P(\Delta E) = \exp^{-[(\Delta E)k*t]}$, where ΔE is a difference in score between the initial structure and the structure derived in (ii) and k is a constant.

In some embodiments, the plurality of structures of the region of the polymer derived by the altering are found using a genetic algorithm. In some embodiments, the plurality of structures derived by altering coordinates is found using a molecular dynamics algorithm.

In some embodiments, the polymer is a protein and the altering alters a side chain of a residue in a subset of residues in the region of the polymer to a rotamer for the side chain found in a rotamer library. In some embodiments, the altering alters a main chain of a residue in a subset of residues in the region of the polymer to a conformation found in a structural library.

In some embodiments, the polymer is a protein and the altering alters a side chain of a residue in a subset of residues in the region of the polymer to a conformation selected from a continuum of conformations for the side chain. In some embodiments, the altering alters a main chain of a residue in a subset of residues in the region of the polymer to a conformation selected from a continuum of main chain conformations.

In some embodiments, the generating step generates a set of clusters in the plurality of sets of clusters for a residue in the polymer using clustering. In some embodiments, the clustering is hierarchical clustering. In some embodiments, the clustering is maximal linkage agglomerative clustering. In some embodiments, the clustering is agglomerative clustering using (i) a nearest neighbor algorithm, (ii) a farthest-neighbor algorithm, (iii) an average linkage algorithm, (iv) a centroid algorithm, or (v) a sum-of-squares algorithm. In some embodiments, the clustering is k-means clustering, fuzzy k-means clustering, Jarvis-Patrick clustering, or steepest descent clustering.

In some embodiments, the method further comprises displaying a representation of the structures in each subgroup in the plurality of subgroups and receiving a selection of a subgroup in the plurality of subgroups. Then, a representation of the structures of the selected subgroup is used as a basis for as an initial set of three-dimensional coordinates and the above identified steps are repeated.

Another aspect provides a computer system for identifying a thermodynamically relevant conformation for a polymer comprising a plurality of atoms. The computer system comprises at least one processor and memory storing at least one program for execution by the at least one processor. The memory further comprises instructions for obtaining an initial set of three-dimensional coordinates $\{x_1, \ldots, x_N\}$ for the polymer, where each respective $x_i$ in $\{x_1, \ldots, x_N\}$ is a three dimensional coordinate for an atom in the plurality of atoms. The memory further comprises instructions for, in silico, replacing one or more residues of the polymer in a region of the polymer with different residues. The memory further comprises instructions for altering a conformation, with respect to the initial set of three-dimensional coordinates $\{x_1, \ldots, x_N\}$ for the polymer, for each respective subset of residues in the region of the polymer in a plurality of subsets of residues in the region of the polymer, of each residue in the respective subset of residues, thereby deriving a plurality of structures of the region of the polymer. Each respective subset of residues in the plurality of subsets of residues in the region of the polymer is selected from among all the residues in the region of the polymer using a deterministic, randomized or pseudo-randomized algorithm. A set of clusters for each respective residue in the region of the polymer using the plurality of structures is generated, thereby creating a plurality of sets of clusters. Each set of clusters in the plurality of sets of clusters can be for a side chain or a main chain of a different residue in the region of the polymer. Alternatively, a set of clusters in the plurality of sets of clusters can be generated for each side chain or a contiguous main chain segment in the region of the polymer under study. A first structure in the plurality of structures is placed in a first cluster in a first set of clusters in the plurality of sets of clusters and a second structure in the plurality of structures is placed in a second cluster in the first set of clusters when a structural characteristic associated with the coordinates of the side chain or the main chain of the residue, represented by the first set of clusters, in the first structure deviates from a structural characteristic associated with the coordinates of the side chain or the main chain of the residue in the second structure by a threshold amount. The respective structures in the plurality of structures are grouped into a plurality of subgroups. Each structure in a subgroup in the plurality of subgroups falls into the same cluster in a threshold number of the sets of clusters in the plurality of sets of clusters. A property is determined for a plurality of structures in a subgroup in the plurality of subgroups, thereby identifying the thermodynamically relevant polymer conformation for the polymer.

Another aspect provides a non-transitory computer readable storage medium storing a computational module for identifying a thermodynamically relevant conformation for a polymer comprising a plurality of atoms. The computational module comprises instructions for obtaining an initial set of three-dimensional coordinates $\{x_1, \ldots, x_N\}$ for the polymer. Each respective $x_i$ in $\{x_1, \ldots, x_N\}$ is a three dimensional coordinate for an atom in the plurality of atoms. In silico, one or more residues of the polymer may be replaced in a region of the polymer with different residues. Alternatively, no residue replacement occurs, and the original primary sequence is used. A conformation is altered, with respect to the initial set of three-dimensional coordinates $\{x_1, \ldots, x_N\}$ for the polymer, for each respective subset of residues in the region of the polymer in a plurality of subsets of residues in the region of the polymer, of each residue in the respective subset of residues, thereby deriving a plurality of structures of the region of the polymer. Each respective subset of residues in the plurality of subsets of residues in the region of the polymer is selected from among all the residues in the region of the polymer using a deterministic, randomized or pseudo-randomized algorithm. A set of clusters is generated for each respective residue in the region of the polymer using the plurality of structures, thereby creating a plurality of sets of clusters. Each set of clusters in the plurality of sets of clusters is for a side chain or a main chain of a different residue in the region of the polymer. A first structure in the plurality of structures is placed in a first cluster in a first set of clusters in the plurality of sets of clusters and a second structure in the plurality of structures is placed in a second cluster in the first set of clusters when a structural characteristic associated with the coordinates of the side chain or the main chain of the residue, represented by the first set of clusters, in the first structure deviates from a structural characteristic associated with the coordinates of the side chain or the main chain of the residue in the second structure by a threshold amount. Respective structures in the plurality of structures are grouped into a plurality of subgroups. Each structure in a subgroup in the plurality of subgroups falls into the same cluster in a threshold number of the sets of clusters in the plurality of sets of clusters. A property of a plurality of structures in a subgroup in the plurality of subgroups is determined, thereby identifying the thermodynamically relevant polymer conformation for the polymer.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIG. 2 illustrates cluster results obtained for each residue i in a polymer by clustering a plurality of structures on a structural characteristic associated with the side chain or the main chain of the $i^{th}$ residue of each respective structure in the plurality of structures in accordance with some embodiments.

FIG. 3 illustrates subgroup results, where each structure in a subgroup falls into the same cluster in a threshold number of the side chain and main chain sets of clusters in a plurality of sets of clusters in accordance with some embodiments.

FIG. 6 illustrates the identity of each cluster that each side chain of each residue in a plurality of polymer structures falls into and the identity of each cluster that each main chain of each residue in the plurality of polymer structures falls into according to some embodiments.

Like reference numerals refer to corresponding parts throughout the several views of the drawings.

DETAILED DESCRIPTION OF THE EMBODIMENTS

The embodiments described herein provide systems and methods for identifying a thermodynamically relevant conformation for a polymer comprising a plurality of atoms.

Figure 1:
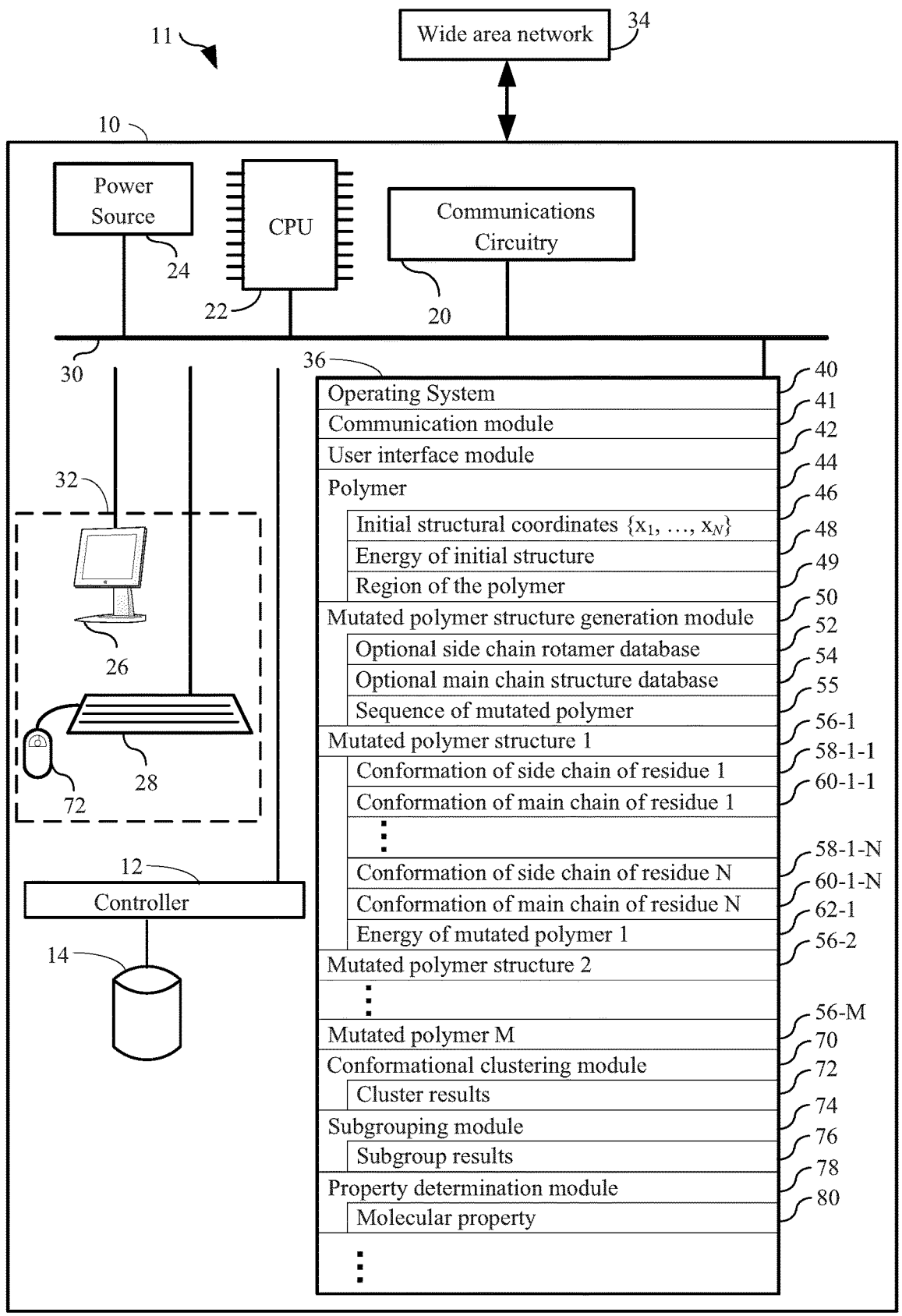
FIG. 1 is a block diagram illustrating a system, according to some embodiments.

FIG. 1 is a block diagram illustrating a computer according to some embodiments. The computer 10 typically includes one or more processing units (CPU's, sometimes called processors) 22 for executing programs (e.g., programs stored in memory 36), one or more network or other communications interfaces 20, memory 36, a user interface 32, which includes one or more input devices (such as a keyboard 28, mouse 72, touch screen, keypads, etc.) and one or more output devices such as a display device 26, and one or more communication buses 30 for interconnecting these components. The communication buses 30 may include circuitry (sometimes called a chipset) that interconnects and controls communications between system components.

Memory 36 includes high-speed random access memory, such as DRAM, SRAM, DDR RAM or other random access solid state memory devices; and typically includes non-volatile memory, such as one or more magnetic disk storage devices, optical disk storage devices, flash memory devices, or other non-volatile solid state storage devices. Memory 36 optionally includes one or more storage devices remotely located from the CPU(s) 22. Memory 36, or alternately the non-volatile memory device(s) within memory 36, comprises a non-transitory computer readable storage medium. In some embodiments, memory 36 or the computer readable storage medium of memory 36 stores the following programs, modules and data structures, or a subset thereof:

- an operating system 40 that includes procedures for handling various basic system services and for performing hardware dependent tasks;
- an optional communication module 41 that is used for connecting the computer 10 to other computers via the one or more communication interfaces 20 (wired or wireless) and one or more communication networks 34, such as the Internet, other wide area networks, local area networks, metropolitan area networks, and so on;
- an optional user interface module 42 that receives commands from the user via the input devices 28, 72, etc. and generates user interface objects in the display device 26;
- a polymer data record 44 that includes (i) initial structural coordinates $\{x_1, \ldots, x_N\}$ 46 for the polymer comprising a plurality of atoms, where the initial structural coordinates $\{x_1, \ldots, x_N\}$ comprise coordinates for all or a portion the heavy atoms in the plurality of atoms and may include all or a portion of the hydrogen atoms in the plurality of atoms, (ii) a score 48 of the initial structure, and (iii) an identification of a region of the polymer 49;
- a mutated polymer structure generation module 50 that comprises instructions for replacing, in silico, the side chain or main chain of one or more residues of the polymer 44 in the region of the polymer 49 with different conformations, optionally using a side chain rotamer database 52 and/or an optional main chain structure database 54; the mutated polymer structure generation module 50 further including the primary sequence of the mutated polymer 55 which consists of the polymer 44 in which one or more residues have been substituted, where a mutation is understood to include the identity mutation (which keeps the type of a residue constant, but may alter the coordinates of the atoms comprising the residue);
- a plurality of mutated polymer structures 56, each mutated polymer structure 56 having the primary sequence of mutated polymer 55 and each mutated polymer structure being generated by the mutated polymer structure generation module 50;
- a conformational clustering module 70 that comprises instructions, for each respective residue i in the polymer 44, of (i) clustering the plurality of mutated structures 56 based on a structural characteristic associated with the side chain of the $i^{th}$ residue of each respective structure in the plurality of structures, thereby deriving a set of side chain clusters for the respective $i^{th}$ residue, (ii) optionally, clustering the plurality of mutated polymer structures 56 based on a structural characteristic associated with the main chain of the $i^{th}$ residue of each respective structure in the plurality of structures, thereby deriving a set of main chain clusters for the $i^{th}$ residue, thereby deriving cluster results 72 and (iii) in place of (ii) optionally clustering the plurality of mutated polymer structures 56 based on a structural characteristic associated with the main chain coordinates of a contiguous main chain segment in the plurality of mutated polymer structures 56;

a subgrouping module 74 for grouping respective structures in the plurality of structures into a plurality of subgroups, where each structure in a subgroup in the plurality of subgroups falls into the same cluster in a threshold number of the side chain and main chain sets of clusters in the plurality of sets of clusters in cluster results 72; and a property determination module 78 for determining a molecular (e.g., thermodynamic) property of a plurality of mutated polymer structures 56 in all or a portion of the subgroups in the subgroup results 76, thereby identifying a thermodynamically relevant polymer conformation for the polymer 46.

In some embodiments, the polymer 44 comprises between 2 and 5,000 residues, between 20 and 50,000 residues, more than 30 residues, more than 50 residues, or more than 100 residues. In some embodiments, a residue in the polymer comprises two or more atoms, three or more atoms, four or more atoms, five or more atoms, six or more atoms, seven or more atoms, eight or more atoms, nine or more atoms or ten or more atoms. In some embodiments the polymer 44 has a molecular weight of 100 Daltons or more, 200 Daltons or more, 300 Daltons or more, 500 Daltons or more, 1000 Daltons or more, 5000 Daltons or more, 10,000 Daltons or more, 50,000 Daltons or more or 100,000 Daltons or more.

In some embodiments, the programs or modules identified above correspond to sets of instructions for performing a function described above. The sets of instructions can be executed by one or more processors (e.g., the CPUs 22). The above identified modules or programs (e.g., sets of instructions) need not be implemented as separate software programs, procedures or modules, and thus various subsets of these programs or modules may be combined or otherwise re-arranged in various embodiments. In some embodiments, memory 36 stores a subset of the modules and data structures identified above. Furthermore, memory 36 may store additional modules and data structures not described above.

Figure 4A:
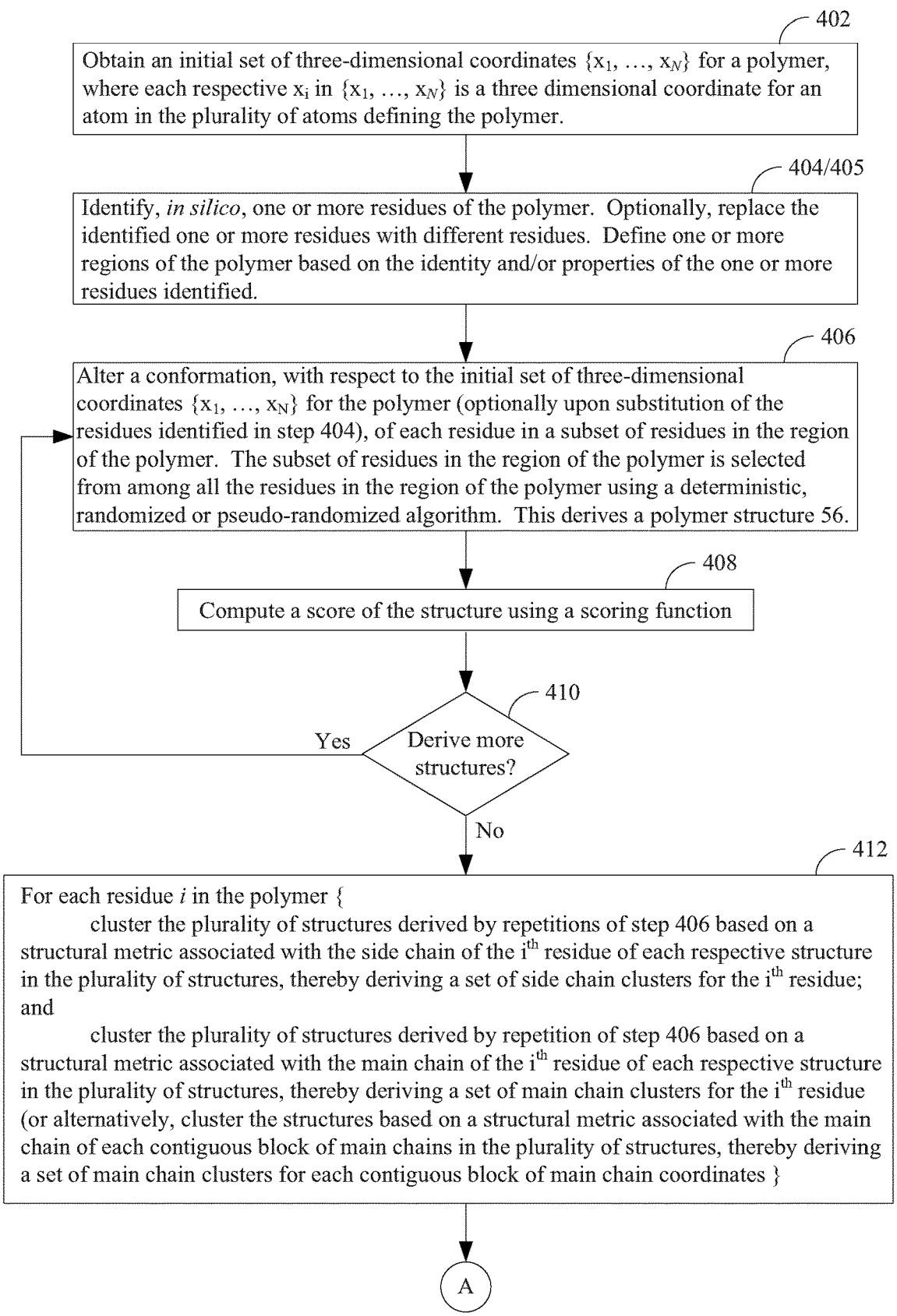
FIGS. 4A and 4B illustrate a method of identifying thermodynamically relevant conformations for a polymer comprising a plurality of atoms according to some embodiments.
Figure 4B:
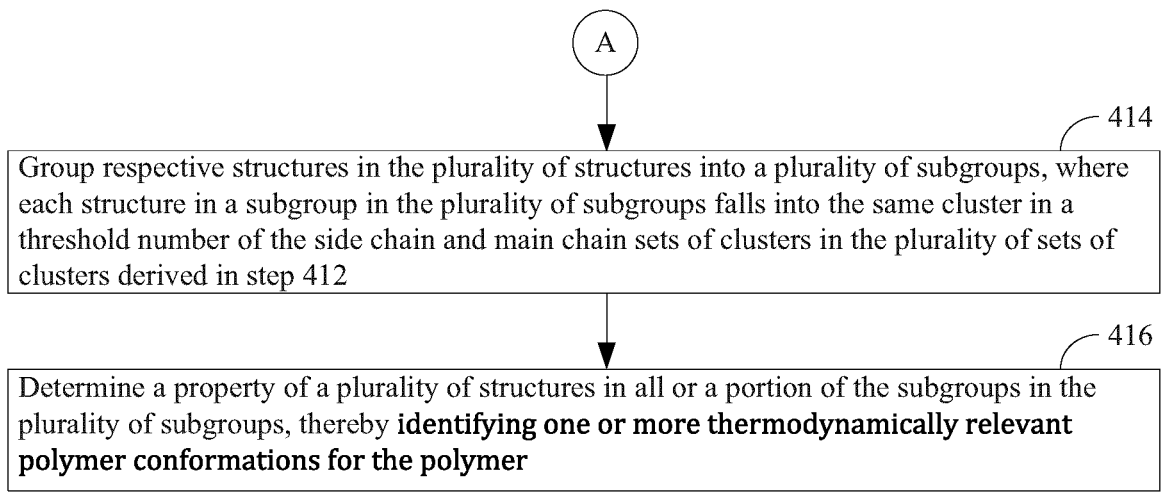

Now that a system in accordance with the systems and methods of the present disclosure has been described, attention turns to FIG. 4 which illustrates an exemplary method in accordance with the present disclosure.

Step 402.

In step 402, an initial set of three-dimensional coordinates $\{x_1, \ldots, x_N\}$ 46 is obtained for a polymer 44. In one example, the polymer 44 is a polynucleic acid and each coordinate $x_i$ in the set $\{x_1, \ldots, x_N\}$ is that of a heavy atom (i.e., any atom other than hydrogen) in the polynucleic acid. In another example, the polymer 44 is a polyribonucleic acid and each coordinate $x_i$ in the set $\{x_1, \ldots, x_N\}$ is that of a heavy atom in the polyribonucleic acid. In still another example, the polymer 44 is a polysaccharide and each coordinate $x_i$ in the set $\{x_1, \ldots, x_N\}$ is that of a heavy atom in the polysaccharide. In still another example, the polymer 44 is a protein and each coordinate $x_i$ in the set of $\{x_1, \ldots, x_N\}$ coordinates is that of a heavy atom in the protein. The set $\{x_1, \ldots, x_N\}$ may further include the coordinates of hydrogen atoms in the polymer 44.

A polymer is a large molecule composed of repeating structural units. These repeating structural units are termed residues herein. In some embodiments, the polymer is a synthetic material. In some embodiments, the polymer 44 is an elastomer, shellac, amber, natural or synthetic rubber, cellulose, BAKELITE, NYLON, polystyrene, polyethylene, polypropylene, or polyacrylonitrile, polyethylene glycol, or polysaccharide.

In some embodiments, the polymer 44 is a heteropolymer (copolymer). A copolymer is a polymer derived from two (or more) monomeric species, as opposed to a homopolymer where only one monomer is used. Copolymerization refers to methods used to chemically synthesize a copolymer. Examples of copolymers include, but are not limited to, ABS plastic, SBR, nitrile rubber, styrene-acrylonitrile, styrene-isoprene-styrene (SIS) and ethylene-vinyl acetate. Since a copolymer consists of at least two types of constituent units (also structural units, or particles), copolymers can be classified based on how these units are arranged along the chain. These include alternating copolymers with regular alternating A and B units. See, for example, Jenkins, 1996, "Glossary of Basic Terms in Polymer Science," Pure Appl. Chem. 68 (12): 2287-2311, which is hereby incorporated herein by reference in its entirety. Additional examples of copolymers are periodic copolymers with A and B units arranged in a repeating sequence (e.g. (A-B-A-B-B-A-A-A-A-B—B-B)$_n$). Additional examples of copolymers are statistical copolymers in which the sequence of monomer residues in the copolymer follows a statistical rule. If the probability of finding a given type monomer residue at a particular point in the chain is equal to the mole fraction of that monomer residue in the chain, than the polymer may be referred to as a truly random copolymer. See, for example, Painter, 1997, *Fundamentals of Polymer Science*, CRC Press, 1997, p 14, which is hereby incorporated by reference herein in its entirety. Still another example of copolymers are block copolymers comprising two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively.

In some embodiments, the polymer 44 is in fact a plurality of polymers, where the plurality of polymers do not all have the same molecular weight. In such embodiments, the plurality of polymers fall into a weight range with a corresponding distribution of chain lengths. In some embodiments, the polymer is a branched polymer molecule comprising a main chain with one or more substituent side chains or branches. Types of branched polymers include, but are not limited to, star polymers, comb polymers, brush polymers, dendronized polymers, ladders, and dendrimers. See, for example, Rubinstein et al., 2003, *Polymer physics*, Oxford; New York: Oxford University Press. p. 6, which is hereby incorporated by reference herein in its entirety.

In some embodiments, the polymer 44 is a polypeptide. As used herein, the term "polypeptide" means two or more amino acids or residues linked by a peptide bond. The terms "polypeptide" and "protein" are used interchangeably and include oligopeptides and peptides. An "amino acid," "residue" or "peptide" refers to any of the twenty standard structural units of proteins as known in the art, which include imino acids, such as proline and hydroxyproline. The designation of an amino acid isomer may include D, L, R and S. The definition of amino acid includes nonnatural amino acids. Thus, selenocysteine, pyrrolysine, lanthionine, 2-aminoisobutyric acid, gamma-aminobutyric acid, dehydroalanine, ornithine, citrulline and homocysteine are all considered amino acids. Other variants or analogs of the amino acids are known in the art. Thus, a polypeptide may include synthetic peptidomimetic structures such as peptoids. See Simon et al., 1992, Proceedings of the National Academy of Sciences USA, 89, 9367, which is hereby incorporated by reference herein in its entirety. See also Chin et al., 2003, Science 301, 964; and Chin et al., 2003, Chemistry & Biology 10, 511, each of which is incorporated by reference herein in its entirety.

A polypeptide may also have any number of posttranslational modifications. Thus, a polypeptide includes those that are modified by acylation, alkylation, amidation, biotinylation, formylation, γ-carboxylation, glutamylation, glycosylation, glycylation, hydroxylation, iodination, isoprenylation, lipoylation, cofactor addition (for example, of a heme, flavin, metal, etc.), addition of nucleosides and their derivatives, oxidation, reduction, pegylation, phosphatidylinositol addition, phosphopantetheinylation, phosphorylation, pyroglutamate formation, racemization, addition of amino acids by tRNA (for example, arginylation), sulfation, selenoylation, ISGylation, SUMOylation, ubiquitination, chemical modifications (for example, citrullination and deamidation), and treatment with other enzymes (for example, proteases, phosphotases and kinases). Other types of posttranslational modifications are known in the art and are also included.

In some embodiments, the polymer 44 is complexed with one or more molecules or atoms, such as metals, cofactors, ions, salts, or water molecules. In some embodiments, the polymer 44 includes one or more metal ions (e.g. a metalloproteinase with a one or more zinc atoms) and/or is bound to one or more organic small molecules (e.g., an inhibitor). In such instances, the metal ions and/or the organic small molecules may be represented by one or more additional coordinates in the set of $\{x_1, \ldots, x_N\}$ coordinates representing the polymer 44.

In some embodiments, the initial structural coordinates $\{x_1, \ldots, x_N\}$ 46 for the complex molecule of interest are obtained by x-ray crystallography, nuclear magnetic resonance spectroscopic techniques, or electron microscopy. In some embodiments, the initial set of three-dimensional coordinates $\{x_1, \ldots, x_N\}$ 46 is obtained by modeling (e.g., molecular dynamics simulations). In typical embodiments, each coordinate in $\{x_1, \ldots, x_N\}$ is a coordinate in three dimensional space (e.g., x, y z).

In some embodiments, there are ten or more, twenty or more, thirty or more, fifty or more, one hundred or more, between one hundred and one thousand, or less than 500 residues in the polymer 44.

Steps 404 and 405.

In step 404, a residue of the polymer 44 in a region of the polymer is identified, in silico, and is optionally replaced with a different residue. In fact, in step 404, more than one residue in a region of the polymer can be identified. In practice, one or more residues of the polymer 44 are identified in the initial structural coordinates $\{x_1, \ldots, x_N\}$ 46. The identified one or more residues are either replaced with different residues and/or they are not replaced and the wild type identity of the residues is maintained. In step 405, one or more regions of the polymer are defined based on the identity and/or properties of the residues identified in step 404.

In one embodiment, a single residue of the polymer 44 is identified, and optionally replaced with a different residue and the region of the polymer is defined as a sphere having a predetermined radius, where the sphere is centered either on a particular atom of the identified residue (e.g., $C_\alpha$ carbon in the case of proteins) or the center of mass of the identified residue. In some embodiments, the predetermined radius is five Angstroms or more, 10 Angstroms or more, or 20 Angstroms or more. For example, in one embodiment, the polymer 44 is a protein comprising 200 residues and an alanine at position 100 (i.e., the $100^{th}$ residues of the 200 residue protein) that is found in the polymer 44 is changed to a tyrosine (i.e., A100W). Then, the region of polymer 49 is defined based on the position of A100W. In some embodiments, the region of the polymer is the $C_{alpha}$ carbon or a designated main chain atom of residue 100 either before or after the side chain has been replaced.

In some embodiments, more than two residues are identified and the region of the polymer 49 in fact is more than two regions. For example, in some embodiments, the polymer is a protein, two different residues are identified, and the region of the polymer 49 comprises (i) a first sphere having a predetermined radius that is centered on the $C_{alpha}$ carbon of the first identified residue and (ii) a second sphere having a predetermined radius that is centered on the $C_{alpha}$ carbon of the second identified residue. Depending on how close the two substitutions are, the residues may or may not overlap. In alternative embodiments, more than two residues are identified, and optionally mutated, and the region is a single contiguous region.

In one embodiment, each residue in a plurality of residues of the polymer 44 is identified in step 404. In some embodiments, this plurality of residues consists of two residues. In some embodiments, this plurality of residues consists of three residues. In some embodiments, this plurality of residues consists of four residues. In some embodiments, this plurality of residues consists of five residues. In some embodiments, this plurality of residues comprises more than five residues. There is no requirement that the plurality of residues be contiguous within the polymer 44. In some embodiments, each respective residue in the plurality of residues is replaced with a different residue. In some embodiments some of the residues in the plurality of residues are replaced with different residues. In some embodiments, none of the residues in the plurality of residues are replaced with different residues. In some of the foregoing embodiments, the region of the polymer 49 is a single region that is defined as a sphere having a predetermined radius, where the sphere is centered at a center of mass of the plurality of identified residues either before or after optional substitution. In some embodiments, the predetermined radius is five Angstroms or more, 10 Angstroms or more, or 20 Angstroms or more. For example, in one embodiment, the polymer 44 is a protein comprising 200 residues and an alanine at position 100 (i.e., the $100^{th}$ residue of the 200 residue protein) that is found in the polymer 44 is changed to a tyrosine (i.e., A100W) and a leucine at position 102 of the polymer 44 is changed to an isoleucine (i.e., L102I). Then, the region of polymer 49 is defined based on the positions of A100W and L102I. In some embodiments, the region of the polymer is the center of mass of A100W and L102I either before or after the mutations have been made.

Step 406.

Step 404 defines a primary sequence of a mutated polymer 55. Throughout this disclosure it will be appreciated that the mutated polymer 55 may in fact have the sequence of the un-mutated polymer 44 because the term "mutated" includes the null mutation where an identified residue is not mutated. The remainder of the steps disclosed in FIG. 4 are designed to identify one or more physical properties of the polymer 55 based on a plurality of three dimensional physical models of the mutated polymer. A three dimensional physical model of the mutated polymer is referred to herein as a mutated polymer structure 56.

The initial structural coordinates $\{x_1, \ldots, x_N\}$, altered, when applicable, to include the side chains of the mutated polymer 55, is the starting point for obtaining the mutated polymer structures 56. An alteration of the conformation, with respect to the starting point structure, of each residue in a subset of residues in the region 49 of the polymer is made. The subset of residues in the region 49 of the polymer is selected from among all the residues in the region 49 of the polymer using a deterministic, randomized or pseudo-randomized algorithm, thereby deriving a structure of the region of the polymer 49.

As one example, consider the case in which the polymer 44 is a protein comprising 200 residues and an alanine at position 100 (i.e., the $100^{th}$ residue of the 200 residue protein) that is found in the polymer 44 is changed to a tyrosine (i.e., A100W). In this example, the region 49 of polymer is defined as those residues that have at least one atom that is within 20 Angstroms of the $C_{alpha}$ carbon of the tyrosine after the A100W substitution. In step 406, one or more residues among those residues that have at least one atom that is within 20 Angstroms of the $C_{alpha}$ carbon of the tyrosine after the A100W substitution is selected for alteration.

In some embodiments, one residue is selected for side-chain conformational alteration from within the region 49 of the polymer in an instance of step 406. In some embodiments, two residues are selected for side-chain conformational alternation from within the region 49 of the polymer in an instance of step 406. In some embodiments, three residues are selected for side-chain conformational alternation from within the region 49 of the polymer in an instance of step 406. In some embodiments, four residues are selected for side-chain conformational alternation from within the region 49 of the polymer in an instance of step 406. In some embodiments, five residues are selected for side-chain conformational alternation from within the region 49 of the polymer in an instance of step 406. In some embodiments, six, seven, eight, nine, or ten residues are selected for side-chain conformational alternation from within the region 49 of the polymer in an instance of step 406. In some embodiments more than ten residues is selected for side-chain conformational alternation from within the region 49 of the polymer in an instance of step 406. In some embodiments, the number and identity of residues that are selected for alteration is determined on a random or pseudo-random basis.

In some embodiments, the conformation of a single residue is altered in step 406. In some embodiments, the conformation of the single residue is altered by either replacing the single residue with the coordinates of a different amino acid type or by leaving the amino acid type of the single residue intact but altering the coordinates of the single residue. The identity of the single residue that is altered in such embodiments can be selected in a random, pseudo-random or deterministic manner.

In some embodiments, step 406 is performed by mutated polymer structure generation module 50.

In some embodiments, the subset of residues that is selected for substitution from within the region 49 of the polymer is done on a deterministic, randomized or pseudo-randomized basis. In some embodiments, the side chain of each residue in the subset of residues that is selected for alteration is altered to a new rotamer. In some embodiments, the new rotamer is selected from a side chain rotamer database (library) 52. Rotamers are usually defined as low energy side chain conformations. The use of optional side chain rotamer database 52 allows for the sampling of the most likely side chain conformations, saving time and producing a structure that is more likely to have lower energy. See, for example, Shapovalov and Dunbrack, 2011, "A smoothed backbone-dependent rotamer library for proteins derived from adaptive kernel density estimates and regressions," Structure 19, 844-858; and Dunbrack and Karplus, 1993, "Backbone-dependent rotamer library for proteins. Application to side chain prediction," J. Mol. Biol. 230: 543-574, Lovell et al., 2000, "The Penultimate Rotamer Library," Proteins: Structure Function and Genetics 40: 389-408, each of which is hereby incorporated by reference herein in its entirety. In some embodiments, the optional side chain rotamer database 52 comprises those referenced in Xiang, 2001, "Extending the Accuracy Limits of Prediction for Side-chain Conformations," *Journal of Molecular Biology* 311, p. 421, which is hereby incorporated by reference in its entirety.

In some embodiments dead end elimination principals are used to reject certain conformations in an instance of step 406. For instance, in some embodiments, a first rotamer for a given side chain of a residue in the polymer is eliminated if any alternative rotamer for the given side chain of the residue in the polymer contributes less to the total energy of the polymer than the first rotamer. In some embodiments this form of dead end elimination principle is used in addition to a Monte Carlo based simulated annealing process to select rotamers for use. Dead end elimination principles are disclosed in Desmet et al., 1992, "The dead-end elimination theorem and its use in protein side-chain position", Nature 356: 539-542; Goldstein, 1994, "Efficient rotamer elimination applied to protein side chains and related spin glasses", Biophys. J. 66: 1335-1340; and Lasters et al., 1995, "Enhanced dead-end elimination in the search for the global minimum energy conformation of a collection of protein side chains", Protein Eng. 8: 815-822; and Leach and Lemon, 1998, "Exploring the Conformational Space of Protein Side Chains Using Dead-End Elimination and the A* Algorithm", Proteins: Structure, Function, and Genetics 33: 227-239 (1998), each of which is hereby incorporated by reference in its entirety.

In some embodiments, the main chain alteration is selected from a main chain structure database 54. In some embodiments the main chain conformation is not altered in step 406.

In another example in accordance with step 406, the search for conformations is coupled with the optimization of side chain degrees of freedom, and makes use of a side chain rotamer database 52. In this example, step 406 is performed by sequentially optimizing each residue in the region 49 of the polymer. Specifically, for a respective residue i in the region 49 of the polymer, the coordinates of the rotamer for the residue type of residue i in the rotamer database 52 is applied to the side chain of residue i in a coordinate set for the polymer. In some instances, the coordinate set to which this rotamer is applied is the initial coordinate set 46 or a set of coordinates 56 from a previous iteration of steps 406 through 412. In other instances, the coordinate set to which this rotamer is applied is the initial coordinate set 46 after the side chains of some of the residues in the region 49 of the polymer have been set to random conformations. In still other instances, the coordinate set to which this rotamer is applied is the initial coordinate set 46 after the side chains of all of the residues in the region 49 of the polymer have been set to random conformations. The main chain coordinates of residue i are held fixed when the rotamer is applied. This rotamer application results in the alteration of the side chain coordinates for residue i in the coordinate set and thus a new conformation in the region 49 of the polymer. In the process of applying the rotamer to residue i, the conformations of the other residues in the region 49 of the polymer are held fixed. In some embodiments, this process of application of the rotamer to a respective residue i to the applicable coordinate set 46 is repeated for each rotamer for the residue type of residue i in the rotamer database 52 thereby resulting in a plurality of coordinates sets for the polymer 44, each coordinate set representing a different rotamer for residue i. To illustrate the example, consider the case in which the residue type of residue i is threonine and the rotamer database 52 in use has three rotamers for threonine, termed the p ($X_1$=59), t ($X_1$=−171), and m ($X_1$=−61) rotamers. In this illustration, three copies of the starting molecular structure are made. The p rotamer is applied to residue i of the first copy of the starting molecular structure, resulting in a first polymer structure 56. The t rotamer is applied to residue i of the second copy of the starting molecular structure, resulting in a second polymer structure 56. The m rotamer is applied to residue i of the third copy of the starting molecular structure, resulting in a third polymer structure 56.

Step 408.

In step 408 a score of a mutated polymer structure 56 constructed in step 406 is calculated using a scoring function. If the step 406 created several mutated polymer structures 56, each of the structures is scored. The score can be computed using any one of several possible functions. As an example, process control can loop over every respective atom in the mutated polymer structure 56 and compute, for example, the coulomb interaction and/or van der Waals interaction between the respective atom and every other atom in the structure, with the interaction between any two atoms being only computed once in preferred embodiments. As a matter of practice, in some embodiments the all-atom potential (force field) developed for use in the AMBER molecular dynamics package, or variants thereof, is used in some embodiments to compute the score of the mutated polymer structure. See for example, Cornell et al., 1995, "A Second Generation Force Field for the Simulation of Proteins," Nucleic Acids, and Organic Molecules", J. Am. Chem. Soc. 117: 5179-5197, which is hereby incorporated by reference herein in its entirety. However, the variety of scoring functions that can be employed in step 408 is large. For example, a statistical potential that returns a value based only on the relative distances between a subset of the atoms on each residue in the mutated polymer structure 56 can be used. This could be supplemented with a potential that returns a value based on the relative spatial orientation of the residues. As such, there are a considerable number of possible scoring functions all of which are within the scope of the present disclosure. Moreover, while in some instances the scoring function provides a score in terms of an "energy", the score returned by a scoring function need not correspond directly to a physical quantity.

In instances where step 406 generated a plurality of polymer structures, each respective polymer structure in the plurality of polymer structures being for a corresponding rotamer of a given residue i, each such polymer structure is scored and the side chain coordinates for the rotamer of residue i that are associated with the most favorable score are identified. The coordinates of the polymer structure containing this most favorable rotamer are retained as a possible thermodynamically relevant alternative conformation of the polymer. Step 410. In step 410, a determination is made as to whether to derive more mutated polymer structures 56 having the sequence of mutated polymer 55. Moreover, in some embodiments, when a decision is made to derive another mutated polymer structure 56 (410—Yes), a further decision is made as to which set of coordinates to use as the starting set of coordinates for this mutated polymer structure 56. These options include using the coordinates of the mutated polymer structure 56 generated in any of the previous instances of step 406 or the initial structural coordinates 46.

In some embodiments in which step 406 was used to generate a plurality of polymer structures, each respective polymer structure in the plurality of polymer structures being for a corresponding rotamer of a residue i, a decision is made to derive another mutated polymer structure 56 (410—Yes) for the next residue (i+1) in the region 49 of the polymer. In some embodiments, the starting point structure that is used for the optimization of residue i+1 are the coordinates of the mutated polymer containing the most favorable rotamer for residue i. Subsequently, in another instance of step 408, the coordinates of the polymer structure containing the most favorable rotamer at position (i+1) are retained as a possible thermodynamically relevant alternative conformation of the polymer. In this manner, steps 406 and 408 are performed for each residue in the region 49 of the polymer until all residues have been tested. Each $n^{th}$ instance of steps 406 and 408, in such embodiments, uses the most favorable coordinates from the $(n-1)^{th}$ instance of steps 406 and 408. The order in which residues in the region 49 of the polymer are selected for such rotamer analysis with steps 406 and 408 is chosen at random prior to optimizing any residue. Once all residues in the region 49 of the polymer have been optimized by steps 406 and 408, a new random ordering of the residues is generated, and the procedure of sequentially polling each rotamer position of each residue in region 49 of the polymer is repeated. The sequential optimization terminates when rotamer re-optimization of all residues in the polymer region does not result in a change in the rotamer conformation of any side chain. The last conformation of the polymer region is considered to be the optimal conformation of the polymer region, and the score of this conformation is considered to be the optimal score. This results in the identification of a single set of coordinates for the mutated polymer structure. However, the single set of coordinates for the mutated polymer structure forms this basis for selecting a plurality of coordinates for the mutated polymer structure. In some embodiments, this is done by iterating over each residue i in the region of the polymer 49 and, for that residue i, cycling through each rotamer for the residue type of residue i in the side chain rotamer base while holding all other residue side chains fixed in the conformation found in the optimal conformation of the polymer region. Each unique conformation of the polymer resulting from the application of a side chain rotamer to residue i from rotamer database 52 is scored. If the difference between this score and the optimal score (e.g., the score of the optimal polymer structure that is being used to generate the plurality of structures) satisfies a threshold value (e.g., a difference between the energy of the unique conformation and optimal conformation is less than a predetermined energy cutoff), the unique conformation is added to the set of possible thermodynamically relevant alternate conformations. After all rotamers have been applied to all residues in the region 49 of the polymer, the search and optimization process terminates in step 410.

In some embodiments steps 406 through 410 are coupled together as part of a refinement algorithm that is directed to finding a mutated structure 56 with lower energy. Such refinement algorithms include simulated annealing and genetic algorithms. As such, repetition of steps 406 through 410 raise the possibility of using starting coordinates that deviate substantially from those of the initial coordinates available at the end of steps 402 or 404. Moreover, by allowing a decision process in which it is possible to use a particularly well scoring structure as the starting point for a new instance of step 406, it is possible to lock in, at least temporarily, favorable rotamer conformations for one or more residues in the region of the polymer while exploring rotamer conformations for other residues in the region of the polymer on a random or pseudorandom basis.

Figure 5:
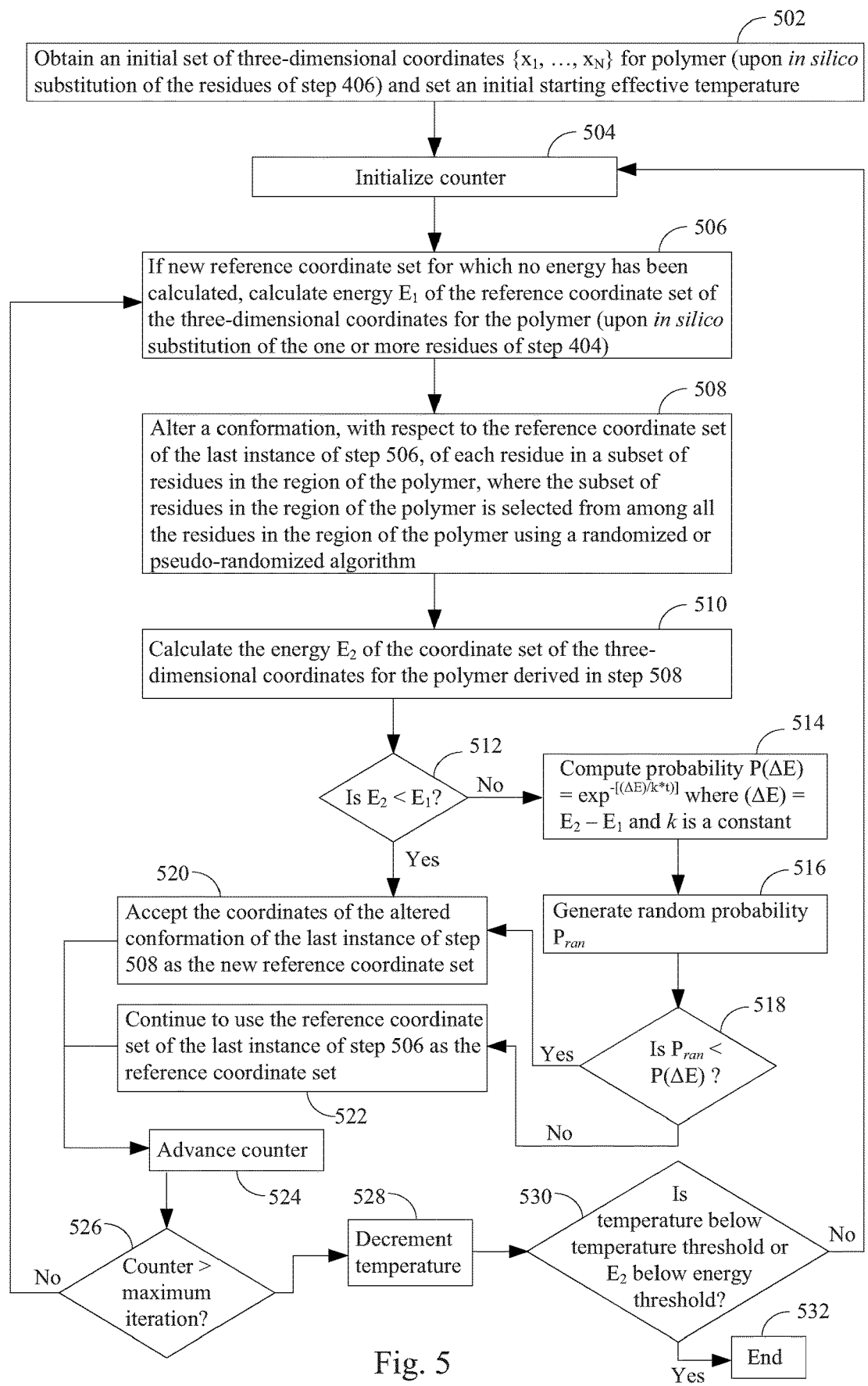
FIG. 5 illustrates a method of identifying polymer structures using simulated annealing according to some embodiments.

FIG. 5 illustrates one such embodiment of steps 406 through 410 of FIG. 4 in which mutated polymer structures, each having the primary sequence of mutated polymer 56 derived in step 404, are created in a manner where it is possible to use a structure derived in a previous instance of step 406 as the starting structure in a new instance of step 406 rather than the coordinates from step 404, under certain circumstances. In step 502, the initial set of coordinates $\{x_1, \ldots, x_N\}$ for the polymer 44, upon in silico substitution of the residues of step 406, is obtained. In the second phase of processing step 502, an initial starting temperature is chosen. The use of an initial starting temperature to obtain better heuristic solutions to a combinatorial optimization problem has its roots in the work of Kirkpatrick et al., 1983, Science 220, 4598. Kirkpatrick et al. noted the methods used to find the low-energy state of a material, in which a single crystal of the material is first melted by raising the temperature of the material. Then, the temperature of the material is slowly lowered in the vicinity of the freezing point of the material. In this way, the true low-energy state of the material, rather than some high energy-state, such as a glass, is determined. Kirkpatrick et al. noted that the methods for finding the low-energy state of a material can be applied to other combinatorial optimization problems if a proper analogy to temperature as well as an appropriate probabilistic function, which is driven by this analogy to temperature, can be developed. The art has termed the analogy to temperature an effective temperature. It will be appreciated that any effective temperature t may be chosen in processing step 502. One of skill in the art will further appreciate that the refinement of an objective function using simulated annealing is most effective when high effective temperatures are chosen. There is no requirement that the effective temperature adhere to any physical dimension such as degrees Celsius, etc. Indeed, the dimensions of the effective temperature t used in the simulated annealing schedule adopts the same units as the objective function that is the subject of the optimization.

In some embodiments, the starting value for the effective temperature is selected based on the amount of resources available to compute the simulated annealing schedule. In still another embodiment, the starting value for the effective temperature is related to the form of the probability function used in processing step 514. It has been found, in fact, that the effective temperature does not have to be very large to produce a substantial probability of keeping a worse score. Therefore, in some embodiments, the starting effective temperature is not large.

Once an initial set of three-dimensional coordinates $\{x_1, \ldots, x_N\}$ for a polymer (upon in silico substitution of the residues of step 406) and an initial starting effective temperature has been selected, an iterative process begins. A counter is initialized in processing step 504. In processing step 506, a score ($E_1$) for a scoring function, such as any of those disclosed in step 408 above, is calculated if there is a new reference coordinate set for which no score has been calculated. In the first instance of step 506, the new coordinate set is the initial set of three-dimensional coordinates $\{x_1, \ldots x_N\}$ obtained in step 502 upon in silico substitution of the residues in step 406. In subsequent instances of step 506, the identity of the new reference coordinate set is dictated by further processing steps as disclosed below.

After a score ($E_1$) of the new reference coordinate set has been determined in step 506, process control passes to step 508 in which a conformation, with respect to the reference coordinate set of step 506, of each residue in a subset of residues in the region of the polymer is altered. The subset of residues in the region of the polymer is selected from among all the residues in the region of the polymer using a deterministic, randomized or pseudo-randomized algorithm. In some embodiments, this algorithm is a Monte Carlo algorithm. Then, in step 510, a score ($E_2$) of the coordinate set of the three-dimensional coordinates for the polymer derived in the last instance of step 508 is calculated using the scoring function that was used to score the initial coordinate set. When the score of the coordinate set derived in step 508 is less than that of the reference coordinate set of step 506 ($E_2 < E_1$) (512—Yes), the coordinates derived in the last instance of step 508 are used as the new reference coordinate set (520). Otherwise (512—No), the coordinates derived in the last instance of step 508 is accepted as the new reference coordinate set with some probability, such as $\exp^{-[(\Delta E)/k^*T]}$. In some embodiments, such as when the probability is $\exp^{-[(\Delta E)/k_*T]}$, the probability that the coordinates derived in the last instance of step 508 is accepted as the new reference coordinate set, when ($E_2 > E_1$), is lower at lower effective temperatures. Use of the exemplary probability function $1 - \exp^{-[(\Delta E)/k^*T]}$ is illustrated as processing steps 514 through 522 in FIG. 5. It will be appreciated that other probability functions $P(\Delta)$ other than $\exp^{-[(\Delta E)/k^*T]}$ could be used and all such functions are within the scope of the present disclosure. In processing step 514, the expression $\exp^{-[(\Delta E)/k^*T]}$ is computed. In processing step 516, a number $P_{ran}$ ran in the interval 0 to 1 is generated. If $P_{ran}$ is less than $P(\Delta E)$ (518—Yes), the coordinates of the altered conformation of the last instance of step 508 is accepted as the new reference coordinate set. If $P_{ran}$ is more than $\exp^{-[(\Delta E)/k^*T]}$ (518—No), the reference coordinate set of the last instance of step 506 is retained as the reference coordinate set (522).

Acceptance of conditions ($E_2 \geq E_1$) for use as a new reference coordinate set on a limited probabilistic basis is advantageous because it provides the refinement system with the capability of escaping local minima traps that do not represent a global solution to the objective function. One of skill in the art will appreciate, therefore, that probability functions other than $\exp^{-[(\Delta E)/k^*T]}$ will advance the goals of the present disclosure. Representative probability functions include, for example, functions that are linearly or logarithmically dependent upon effective temperature, in addition to those that are exponentially dependent on effective temperature.

In some embodiments, the three-dimensional coordinates for the polymer derived in the last instance of step 508 are recorded when (i) their energy $E_2$ has been accepted (e.g., when simulated annealing is used either because $E_2$ is less than $E_1$ or on a probabilistic basis when $E_2$ is greater than $E_1$ as set forth above) and (ii) $E_2 - E_{min} < E_0$, where $E_0 \geq 0$ is a predetermined, but arbitrary, threshold value, and $E_{min}$ is the energy of the lowest energy accepted for a configuration of the polymer encountered up to and including the current iteration of the refinement algorithm. It will be appreciated that these conditions for recording the three-dimensional coordinates, $E_2$ accepted and $E_2 - E_{min} < E_0$ for the polymer can be used when refinement algorithms other than simulated annealing (such as genetic algorithms) are used as well.

Processing steps 506 through 522 represent one iteration in the refinement process illustrated in FIG. 5. In processing step 524 an iteration count is advanced. When the iteration count does not exceed the maximum iteration count (526—No), the process continues at 506. When the iteration count equals a maximum iteration flag (526—Yes), effective temperature t is reduced (528). One of skill in the art will appreciate that there are many different types of schedules that are used to reduce effective temperature t in various embodiments of processing step 528. All such schedules are within the scope of the present disclosure. In one embodiment, effective temperature t is reduced in step 528 by one, two, three, four, five, six, seven, eight, nine, ten, eleven, twelve, thirteen, fourteen, or fifteen percent. In another embodiment, effective temperature t is reduced by a constant value. For example, the effective temperature could be reduced by 50, 100, 150, 200, 250, 300, 350, 400, 450, or 500 Kelvin each time processing step 528 is executed.

When the effective temperature has been reduced by an amount in processing step 528, a check is performed to determine whether the simulated annealing schedule should be terminated (530). In the embodiment illustrated in FIG. 5, the process is terminated (530—Yes, 532) when effective temperature t has fallen below a low effective temperature threshold or $E_2$ falls below a predetermined score. In typical embodiments, a predetermined score for $E_2$ is generally not available. Generally the algorithm runs to the specified minimum temperature, for the specified number of cycles, and no termination criterion is applied to $E_2$. In some embodiments, a termination criterion is applied to $E_2$ that specifies termination (530—No) if the number of cycles between the present iteration of the algorithm and the last time $E_2$ was less than $E_{min}$ is greater than some threshold number of iterations c. For instance, if $E_{min}$ is fifteen relative energy units and c is five iterations, the process would terminate when five iterations in a row failed to achieve an $E_2$ that was less than $E_{min}$.

The low effective temperature threshold is any suitably chosen effective temperature that allows for a sufficient number of iterations of the refinement cycle at relatively low effective temperatures. When it is determined that the annealing schedule should not end (530—No), process control passes to step 504 with the reinitialization of the counter back to a starting value so that a counter toward maximum iteration can begin again.

In another embodiment of the present disclosure, a distinctly different exit condition than the one illustrated in FIG. 5 is used. In this alternative embodiment, a separate counter is maintained. This counter, which could be termed a stage counter, is incremented each time the effective temperature is reduced in step 528. When the stage counter has exceeded a predetermined value, such as fifty, the simulating annealing process ends (532). In yet another embodiment, a counter tracks a consecutive number of times the coordinate set of step 508 is rejected. When a set number of arbitrary changes in a row have been rejected, the process ends (532).

Step 412.

Returning to FIG. 4, the net result of steps 406 through 410, optionally implemented as steps 502 through 532 of FIG. 5, is a plurality of stored mutated polymer structures 56 each having the primary sequence of mutated polymer 55. In some embodiments, steps 406 through 410 produce one hundred or more, two hundred or more, three hundred or more, five hundred or more, one thousand or more, ten thousand or more, one hundred thousand or more or 1 million or more mutated polymer structures 56 each having the primary sequence of mutated polymer 55. In step 412, these mutated polymer structures are clustered on a residue by residue basis.

In instances where large rotamer libraries are used in steps 406 through 410, or the steps operate in continuous space (e.g., continuum space Monte Carlo), a very large number of mutated polymer structures in which there are only slightly different configurations with slightly different energies will be generated. One could sum over all of these structures and derive thermodynamic properties out of the structures. However, the objective is to assist in understanding structurally the effects of the mutations of step 404. So, the set of mutated polymer structures 56 is reduced in step 412 to a set of meaningfully distinct structural conformations. For instance, consider the case in which there are two mutated polymer structures 56 that only differ by half a degree in a single terminal dihedral angle. Such structures are not deemed to be meaningfully distinct and therefore fall into the same cluster in some embodiments of the present disclosure.

Advantageously, the present disclosure provides for reducing the plurality of mutated polymer structures 56 into a reduced set of structures without losing information about meaningfully distinct conformations found in the plurality of mutated polymer structures 56. This is done in some embodiments by clustering on side chains individually and the backbone individually (e.g., on a residue by residue basis). This is done in other embodiments by (i) clustering on side chains individually and (ii) separately clustering based on a structural metric associated with the main chain of each contiguous block of main chains in the plurality of structures, thereby deriving a set of main chain clusters for each contiguous block of main chain coordinates. Regardless of which embodiment is done, if there is a meaningful shift in any side chain or any backbone between two of the mutated polymer structures 56, even if the two structures are otherwise structurally very similar, the clustering ultimately will not group the two conformations into the same cluster and thus obscure that difference. In some embodiments, the residue by residue clustering imposes a root-mean-square distance (RMSD) cutoff on the coordinates of the subject side chain atoms or the subject main chain atoms. For example, when clustering on a particular residue side chain, two mutated polymer structures 56 will fall into the same cluster for the particular residue side chain when the RMSD between the side chain atoms of the particular side chain in the two mutated polymer structures 56 falls below a predetermined RMSD cutoff value. In some embodiments, this predetermined RMSD cutoff value is 0.2 Angstroms or greater, 0.3 Angstroms or greater, 0.4 Angstroms or greater, 0.5 Angstroms or greater, or 0.6 Angstroms or greater. This RMSD is computed between the side chain of the particular residue after the two mutated polymer structures 56 have been superimposed upon each other using conventional techniques.

Another way of considering the novel approach taken in step 412 is to consider the samplings made in steps 406 through 410 that are made in rotameric space, and consider that the outcome of steps 406 through 410 is that, for each residue in the sequence of the mutated polymer, there is now a list of possible rotamers. If a sufficient number of rotamers is sampled, this list becomes very large for each residue and, in fact, if continuum space is considered, this list can approach infinity for each residue. Thus, in step 412, particularly in the case where continuum space or a large rotamer library is used in steps 406 through 410, what is obtained is the definition of a new rotamer library for each residue; not by residue type but for each residue in the sequence of the mutated polymer 55, where each cluster for each residue is a new rotamer. This can be done for the backbone or some segment of the backbone as well.

Thus, step 412 clusters based on change in conformation, change in RMSD or change in angles, without considering the score of the mutated polymer structures 56. In this way, either the backbone or the side chain of a given residue of a mutated polymer structure 56 could trigger an event in which that conformation together, the backbone and side chain, just simply cannot go into the same cluster as another mutated polymer structure 56.

In some embodiments, the type of clustering that is performed in step 414 on a residue by residue basis, and on each side chain individually and on each main chain individually is maximal linkage agglomerative clustering.

Clustering is described on pages 211-256 of Duda and Hart, *Pattern Classification and Scene Analysis,* 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., *Pattern Classification,* 2$^{nd}$ edition, John Wiley & Sons, Inc. New York, has been published. Pages 537-563 of the reference describe clustering in detail. More information on clustering techniques can be found in Kaufman and Rousseeuw, 1990, *Finding Groups in Data: An Introduction to Cluster Analysis,* Wiley, New York, N.Y.; Everitt, 1993, *Cluster analysis* (3d ed.), Wiley, New York, N.Y.; and Backer, 1995, *Computer-Assisted Reasoning in Cluster Analysis,* Prentice Hall, Upper Saddle River, N.J. Particular exemplary clustering techniques that can be used in step 414 include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, Jarvis-Patrick clustering, and steepest-descent clustering.

In some embodiments in step 414, the plurality of mutated polymer structures 56 are clustered based on the conformation of residue 1 of the mutated polymer 55 in each of the mutated polymer structures 56 to form a first set of clusters. Next, the plurality of mutated polymer structures 56 are separately clustered based on the conformation of residue 2 of the mutated polymer 55 in each of the mutated polymer structures 56 to form a second set of clusters, and so forth to form a set of clusters for each residue in the mutated polymer.

In some embodiments, the plurality of mutated polymer structures 56 is clustered on a residue by residue basis for side chain conformation only. That is, the plurality of mutated polymer structures 56 are clustered based on the conformation of the side chains of residue 1 of the mutated polymer 55 in each of the mutated polymer structures 56 to form a first set of clusters. Next, the plurality of mutated polymer structures 56 are clustered based on the conformation of the side chains of residue 2 of the mutated polymer 55 in each of the mutated polymer structures 56 to form a second set of clusters, and so forth to form a set of clusters for each residue in the mutated polymer where the conformation of the main chain atoms of the polymer did not inform or affect the clustering.

In some embodiments, the plurality of mutated polymer structures 56 are clustered on a residue by residue basis for side chain conformation and, separately, on a residue by residue basis for main chain conformation. That is, the plurality of mutated polymer structures 56 are clustered based on the conformation of the side chains of residue 1 of the mutated polymer 55 in each of the mutated polymer structures 56 to form a first set of clusters. Next, the plurality of mutated polymer structures 56 are clustered based on the conformation of the main chains of residue 1 of the mutated polymer 55 in each of the mutated polymer structures 56 to form a second set of clusters. Next, the plurality of mutated polymer structures 56 are clustered based on the conformation of the side chains of residue 2 of the mutated polymer 55 in each of the mutated polymer structures 56 to form a third set of clusters. Next, the plurality of mutated polymer structures 56 are clustered based on the conformation of the main chains of residue 2 of the mutated polymer 55 in each of the mutated polymer structures 56 to form a fourth set of clusters, and so forth to form two sets of clusters for each residue in the mutated polymer, a main chain set for each residue and a side chain set for each residue.

FIG. 2 illustrates the cluster results 72 that are obtained in this embodiment. For each respective residue in the sequence of the mutated polymer 55, there is a set of clusters 202 for the side chain of the respective residue and a set of clusters 208 for the main chain of the respective residue. Each set of clusters 202 includes one or more clusters 204. Each cluster 204 includes the identity of one or more mutated polymer structures 206 that fall into the cluster. Each set of clusters 208 includes one or more clusters 210. Each cluster 210 includes the identity of one or more mutated polymer structures 206 that fall into the cluster. In alternative embodiments, all main chain coordinates are clustered on contiguous blocks of residues. For example, consider the case in which the polymer comprises an "A" domain and a "B" domain, where the main chain is not contiguous between the "A" domain and the "B" domain and residues in the A domain are designated A/XX whereas residues in the B domain are designated B/XX. If residues A/100-A/110 and residues A/200-A/210 are under consideration (e.g., residues A/100-A/110 and A/200-A/210 constitute the region of the polymer under consideration), all side chain degrees of freedom are clustered and then all the main chain degrees of freedom for residues A/100-A/110 are clustered as a unit, and all main chain degrees of freedom for residues A/200-A/210 are clustered as a unit.

In some embodiments, for a given residue in the mutated polymer structures, mutated polymer structures are placed in the same cluster when the RMSD is less than 1.0 Angstrom for the side chain of the given residue when the given residue is one that does not have mobile hydrogen atoms. In some embodiments, for a given residue in the mutated polymer structures, mutated polymer structures are placed in the same cluster when the RMSD is less than 0.9 Angstroms, less than 0.8 Angstroms, less than 0.7 Angstroms, less than 0.6 Angstroms, less than 0.5 Angstroms, less than 0.4 Angstroms, less than 0.3 Angstroms, or less than 0.2 Angstroms for the side chain of the given residue when the given residue is one that has mobile hydrogen atoms (e.g., serine, threonine, and tyrosine). However, these values can be adjusted to other values any of which are within the scope of the present disclosure.

In some embodiments the threshold used for clustering is determined through an automated training process making use of expert review. In this process, an individual with protein structure expertise is presented with two conformations of a residue of a specific type. The expert is then asked if the two conformations are meaningfully distinct. If the conformations are judged by the expert to be distinct, a second pair of residue conformations is presented to the expert. The difference in structure between the elements of this second pair is chosen to be smaller than the difference in structure between the elements of the first pair. If the expert judged the first pair of structures to be indistinct, the expert is presented with a second pair of residue conformations exhibiting a degree of structural distinctiveness larger than the degree of distinctiveness exhibited by the first pair. The answers provided by the expert to these queries are used to calculate a level of structural distinctiveness at which the expert viewing two conformations of the residue of the specific type having this level of structural distinctiveness will judge the conformations to be structurally distinct and structurally indistinct with equal probability. This level of structural distinctiveness is used as the threshold value for clustering residues of the type presented to the expert. In some embodiments, this process is repeated for each residue type. In some embodiments, in order to reduce the amount of interaction with the expert, the twenty naturally occurring residues are grouped by like composition (e.g., leucine and isoleucine are grouped together) and the process is only repeated for each group of residues rather than for each possible residue type. In some embodiments, the measure of structural distinctiveness is quantified as a root-mean-square deviation (RMSD) between the Cartesian coordinates of the heavy atoms in a residue. In some embodiments the measure of structural distinctiveness is the RMSD between the dihedral angles in a residue. In some embodiments the measure of structural distinctiveness is a metric that comprises a mathematical combination of (i) the RMSD between the dihedral angles in a residue and (ii) the RMSD between the dihedral angles in a residue. This technique is further disclosed in U.S. patent application Ser. No. 61/838,225, entitled "Systems and Methods for Physical Parameter Fitting on the Basis of Manual Review", attorney docket No. 069480-5015-PR, filed Jun. 21, 2013, which is hereby incorporated by reference herein in its entirety.

Step 414.

The result of step 412 is that each residue in each mutated polymer structure 56 is assigned to a cluster group. In typical embodiments, the side chain of each residue in each mutated polymer structure 56 is assigned to a side chain cluster group and the main chain of each residue in each mutated polymer structure 56 is assigned to a main chain cluster group. In step 414, mutated polymer structures 56 in the plurality of mutated polymer structures generated in steps 406 through 410 are grouped together into a plurality of subgroups based on the identity of the clusters that their residues fall into.

FIG. 6 illustrates the concept of step 414. Mutated polymer structure 56-1 consists of residues 1 through N. For each respective residue in each respective mutated polymer structure, there is an identity of the side chain cluster that the respective residue falls into and, optionally, an identity of the main chain cluster that the respective residue falls into. For example, the side chain of residue 1 of the mutated polymer structure 56-1 falls into cluster 204-1-1 in the set of clusters 202-1, the main chain of residue 1 of the mutated polymer structure 56-1 falls into cluster 210-1-7 in the set of clusters 208-1, the side chain of residue 2 of the mutated polymer structure 56-1 falls into cluster 204-2-5 in the set of clusters 202-2, the main chain of residue 2 of the mutated polymer structure 56-1 falls into cluster 210-2-12 in the set of clusters 208-2, and so forth.

Examination of FIG. 6 shows that mutated polymer structures 56-1 and 56-M always fall into the same cluster (204-1-1, 210-1-7, 204-2-5, 210-2-12, . . . , 204-N-1, and 210-N-4) whereas mutated polymer structure 56-2 falls into different clusters (204-1-5, 210-1-3, 204-2-2, 210-2-11, . . . , 204-N-102, and 210-N-6). Thus, in step 414, mutated polymer structures 56-1 and 56-M will be grouped into the same subgroup whereas mutated polymer structure 56-2 will be grouped into a different subgroup.

FIG. 3 illustrates the end result of processing step 414. There is some number of subgroups 302. For each subgroup 302, there is a list of mutated polymer structures 55 having respective side chain and main chain conformations falling into the same respective clusters 204/201 across the plurality of sets of clusters 202/208 that were created in step 412.

In some embodiments, respective mutated polymer structures 56 in the plurality of mutated polymer structures are subgrouped into a plurality of subgroups 302, where each mutated polymer structure 56 in a subgroup 302 in the plurality of subgroups falls into the same cluster 204/210 in a threshold number of the sets of clusters 202/208 in the plurality of sets of clusters generated in step 412. In some embodiments, the threshold number of the sets of clusters 202/208 is all the sets of clusters in the plurality of sets of clusters generated in step 412. In some embodiments, the threshold number of the sets of clusters 202/208 is all but one, all but two, all but three, all but four, all but five, all but six, all but seven, all but eight, all but nine, or all but ten of the sets of clusters 202/208 in the plurality of sets of clusters generated in step 412. In some embodiments, the threshold number of the sets of clusters 202/208 is at least sixty-five percent, at least seventy percent, at least seventy-five percent, at least eighty percent, at least eighty-five percent, at least ninety percent, at least ninety-five percent, at least ninety-seven percent, at least ninety-eight percent or at least ninety-nine percent of the sets of clusters 202/208 in the plurality of sets of clusters generated in step 412. In some embodiments the sets of clusters 202/208 used to create a subgroup 302 is determined on the basis of a property of the polymer with its wild type or mutated sequence. For example clusters 202/208 used to create subgroups 302 can be selected on the basis of residue type, on the basis of solvent accessible surface area in the wild type sequence and configuration, on the basis of residue charge, on the basis of distance from the residue affected by step 404 of FIG. 4, etc.

In some embodiments, the mutated polymer structures 56 are classified into subgroups 76 solely on the basis of how many of their residues fall into the same side chain clusters 204 and main chain clusters 210 are not used to classify mutated polymer structures into subgroups 76. In some embodiments, the mutated polymer structures 56 are classified into subgroups 76 on the combined basis of how many of their residues fall into the same side chain clusters 204 and home many of their residues fall into the same main chain clusters 210.

Step 416.

In step 414, a plurality of subgroups 302 were generated. Each subgroup 302 includes a plurality of mutated polymer structures having the same mutated polymer sequence 55 and similar, but not identical structural conformations. However, typically, each mutated polymer structure in a subgroup 302 will have a different score because, while the conformations within a subgroup 302 are similar, they are not exactly the same.

Because each subgroup 302 comprises several structures rather than just a structure having a minimum score, a partition function can be computed for the structural state represented by a given subgroup 302 and used to determine thermodynamics of the conformation state represented by the given subgroup 302. For instance, a free energy estimate can be computed for the general structural conformation represented by each subgroup 302 in the plurality of subgroups.

In some embodiments, an average is taken over all the structural conformations of the mutated polymer structures mapping into a subgroup 302 and one or more properties of the mutated polymer structures is determined as well as a range for each of the one or more properties. Here, the average can be the arithmetic average, or a thermodynamic average. In some embodiments, the property is a mean distance between two things within the polymer structure, mean distance between a point in the polymer structure and a point on a receptor that the polymer structure binds, etc. It will be appreciated that a property in the one or more properties does not have to be a simple mean. Examples of properties that may be ascertained also include median properties, or properties such as an entropy or variance in structural quantity, to name a few.

In some embodiments, a filter is applied such that subgroups 302 having an average energy that is above a threshold energy are eliminated. In some embodiments, a filter is applied such that subgroups 302 having less than a threshold number for polymer structures are eliminated. However, in some embodiments, even subgroups 302 having fewer than a threshold number of polymer structures are retained when the average energy for such subgroups is sufficiently low. In some embodiments, a subgroup having a low average energy is used as the starting basis for another iteration of steps 406 through 416.

In some embodiments an accessible surface area is computed for an ensemble of structures in a subgroup 302, where the ensemble of structures is treated as a single structure. The accessible surface area (ASA), also known as the "accessible surface", is the surface area of a biomolecule that is accessible to a solvent. Measurement of ASA is usually described in units of square Angstroms. ASA is described in Lee & Richards, 1971, J. Mol. Biol. 55(3), 379-400, which is hereby incorporated by reference herein in its entirety. ASA can be calculated, for example, using the "rolling ball" algorithm developed by Shrake & Rupley, 1973, J. Mol. Biol. 79(2): 351-371, which is hereby incorporated by reference herein in its entirety. This algorithm uses a sphere (of solvent) of a particular radius to "probe" the surface of the molecule.

In some embodiments a solvent-excluded surface is computed for an ensemble of structures in a subgroup 302, where the ensemble of structures is treated as a single structure. The solvent-excluded surface, also known as the molecular surface or Connolly surface, can be viewed as a cavity in bulk solvent (effectively the inverse of the solvent-accessible surface). It can be calculated in practice via a rolling-ball algorithm developed by Richards, 1977, Annu Rev Biophys Bioeng 6, 151-176 and implemented three-dimensionally by Connolly, 1992, J. Mol. Graphics 11(2), 139-141, each of which is hereby incorporated by reference herein in its entirety.

In some embodiments, a physical property that is determined in step 416 is a presence or mean energy of a covalent bond or hydrogen bond between a first atom and a second atom in the ensemble of structures in a subgroup 302. Hydrogen bonds are formed when an electronegative atom approaches a hydrogen atom bound to another electronegative atom. The most common electro negative atoms in biochemical systems are oxygen (3.44) and nitrogen (3.04) while carbon (2.55) and hydrogen (2.22) are relatively electropositive. The hydrogen is normally covalently attached to one atom, the donor, but interacts electrostatically with the other, the acceptor. This interaction is due to the dipole between the electronegative atoms and the proton. Thus, the first atom in the plurality of atoms represented by particle $p_i$ is the donor and the second atom in the plurality of atoms represented by particle $p_j$ is the acceptor of the hydrogen, or vice versa. Moreover, the first atom in the plurality of atoms represented by particle $p_i$ and the second atom in the plurality of atoms represented by particle $p_j$ share the same hydrogen. The occurrence of hydrogen bonds in protein structures has been extensively reviewed by Baker & Hubbard, 1984, Prog. Biophy. Mol. Biol., 44, 97-179, which is hereby incorporated by reference herein in its entirety.

In some embodiments, a physical property that is determined in step 416 is a presence or mean energy of a carbon-carbon contact, a carbon-sulfur contact, or a sulfur-sulfur contact between a first atom and a second atom in the ensemble of structures in a subgroup 302. In some embodiments, a carbon-carbon contact, a carbon-sulfur contact, or a sulfur-sulfur contact occurs when the first atom and the second atom are each independently carbon or sulfur and the first atom and the second atom are within a predetermined distance of each other in the complex molecule. In some embodiments, this predetermined distance is 4.5 Angstroms. In some embodiments, this predetermined distance is 4.0 Angstroms.

In some embodiments, a physical property that is determined in step 416 is a presence or mean energy of a carbon-nitrogen contact between a first atom and a second atom in the ensemble of structures in a subgroup 302. In some embodiments, a carbon-nitrogen contact occurs when the first atom is a carbon and the second atom is a nitrogen and the first atom and the second atom are within a predetermined distance of each other in the complex molecule as defined by the three-dimensional coordinates $\{x_1, \ldots, x_N\}$. In some embodiments, this predetermined distance is 4.5 Angstroms. In some embodiments, this predetermined distance is 4.0 Angstroms. In some embodiments, this predetermined distance is 3.5 Angstroms.

In some embodiments, a physical property that is determined in step 416 is a presence or mean energy of a carbon-oxygen contact between a first atom and a second atom in the ensemble of structures in a subgroup 302. In some embodiments, a carbon-oxygen contact occurs when the first atom is a carbon and the second atom is a oxygen and the first atom and the second atom are within a predetermined distance of each other in the complex molecule. In some embodiments, this predetermined distance is 4.5 Angstroms. In some embodiments, this predetermined distance is 4.0 Angstroms. In some embodiments, this predetermined distance is 3.5 Angstroms.

In some embodiments, a physical property that is determined in step 416 is a presence of or mean energy of a π-π interaction or a π-cation interaction between a first atom and a second atom in the ensemble of structures in a subgroup 302. A π-π interaction is an attractive, noncovalent interaction between aromatic rings in which the aromatic rings are parallel to each other or form a T-shaped configuration and their respective centers of mass are approximately five Angstroms apart. See, for example, Brocchieri and Karlin, 1994, PNAS 91:20, 9297-9301, which is hereby incorporated by reference. A π-cation interaction is a noncovalent molecular interaction between the face of an electron-rich π system (e.g. benzene, ethylene) and an adjacent cation (e.g. $NH_3$ group of lysine, the guanidine group of arginine, etc.). This interaction is an example of noncovalent bonding between a quadrupole (π system) and a monopole (cation).

In some embodiments, a physical property that is determined in step 416 is a measure of structural diversity within each subgroup. An example of a measure of structural diversity is the configurational entropy computed from the partition function created by summing over all members of a subgroup.

EXAMPLE

This example demonstrates the ability of the invention to identify thermodynamically relevant alternate conformations of a protein. The example makes use of an antibody Fc structure (PDB Accession ID 1E4K), herein referred to as the wild type structure. A mutated polymer structure 56 was prepared by mutating residues B/248.LYS, B/249.ASP, B/250.THR in the parent structure to GLY, ARG, and GLY respectively. A region 49 of the muted polymer structure 56 was then defined by enumerating every residue that had a heavy atom with a distance less than 8 Å from any heavy atom of residues B/248-250 in the wild type structure. A random conformation from the rotamer database 52 was subsequently assigned to each of the residues B/248-250 in the mutated polymer structure 56. For this example, the rotamer database 52 comprised the rotamers described in Xiang, 2001, "Extending the Accuracy Limits of Prediction for Side-chain Conformations," *Journal of Molecular Biology* 311, p. 421, which is hereby incorporated by reference in its entirety. This rotamer library was expanded by adding the rotameric conformation observed in the wild type structure of every residue in polymer region 49.

One of the residues in region 49 of the mutated polymer was randomly selected and a rotamer in the rotamer database 52 for the side chain type at the selected residue was applied to the initial mutated polymer structure 56 prepared as described above. The main chain coordinates of the selected residue position were held fixed during application of the rotamer to the selected residue. This application of the rotamer resulted in the alteration of the side chain coordinates for the selected residue in the initial mutated polymer structure 56 and thus a new conformation in the region 49 of the polymer. In the process of applying the rotamer to the selected residue position, the conformations of the other residues in the region 49 of the mutated polymer structure were held fixed. The application of the n rotamers to n corresponding instance of the initial mutated polymer structure 56 resulted in n different structures of the polymer, where n is a positive integer, each different structure representing a different rotamer for the selected residue. The n structures of the polymer were evaluated to determine which had the lowest energy in accordance with step 408. For this energy calculation, the AMBER all-atom potential was used to score the conformations of the optimization region of each of the n structures in the manner disclosed in Ponder and Case, 2003, "Force fields for protein simulations," Adv. Prot. Chem. 66, p. 27, which is hereby incorporated by reference herein in its entirety. The structure of the polymer that had the lowest energy was then used as the starting point for evaluating the rotamers of another residue in the set of residues comprising the polymer region 49 in the same manner as the first residue, thereby identifying a structure of the polymer that had the lowest energy when the rotamers of database 52 for the second residue selected from the set of residues comprising the polymer region 49 were polled in like manner. Once all residues in the polymer region were optimized in this manner, a new random ordering of the residues in the set was generated, and the rotamer search procedure describe above repeated using the final structure for the polymer from the last round (the structure in which the rotamer of the final residue in the set of residues in polymer region 49 has been polled to find the lowest energetic structure). The sequential optimization of rotamers in the set of residues in polymer region 49 terminated when re-optimization of all residues in the polymer region in the sequential iterative manner described above using the side chain rotamer database 52 did not result in a change in the conformation of any side chain. The last conformation of the polymer region was deemed to be the optimal conformation of the polymer region, and the score of this conformation was considered to be the optimal score. This resulted in the identification of a single set of coordinates for the mutated polymer structure.

The above procedure was employed a total of twenty times, with each use of the procedure differing by the random conformations initially assigned to residues B/248-B/250 in the starting structure. Each of the twenty instances yielded a final structure. Each of the final structures was used as a basis to generate additional structures by iterating over each residue i in the set of residues in polymer region 49 and, for that residue i, cycling through each rotamer for the residue type of residue i in the side chain rotamer database 52 while holding all other residue side chains fixed in the conformation found in the optimal conformation of the region 49 of the polymer. Each unique conformation of the polymer resulting from the application of a side chain rotamer to residue i was scored against the corresponding final structure in the twenty instances of the final structure. If the difference between this score and the optimal score satisfied a threshold value, the unique conformation was added to the set of possible thermodynamically relevant alternate conformations.

The conformations of the optimization region 49 produced as described above were then combined to form an aggregate set of alternate conformations. The scores of the optimal conformations produced by the twenty instances of the optimization procedure were compared, and the conformation with the most favorable score was accepted as the most favorable conformation of polymer region 49. It will be appreciated that, because portions of the polymer outside of the region 49 of the polymer are held fixed in this example, structural examination of the region 49 of the polymer is all that is necessary in some steps of the example, such as the clustering described below. The elements of the set of alternate conformations were then clustered and grouped in accordance with step 412. In the clustering step, complete linkage hierarchical clustering was employed, with the root-mean square deviation of the Cartesian coordinates of side chain heavy atoms serving as the distance function. See Izenman, 2008, "Modern Multivariate Statistical Techniques," Springer Science+Business Media LLC, New York N.Y., which is hereby incorporated by reference for its teachings on complete linkage hierarchical clustering. The distance threshold used in clustering was set by the interactive technique disclosed above in step 412 and which is further disclosed in U.S. patent application Ser. No. 61/838,225, entitled "Systems and Methods for Physical Parameter Fitting on the Basis of Manual Review", attorney docket No. 069480-5015-PR, filed Jun. 21, 2013, which is hereby incorporated by reference herein in its entirety. Two structurally distinct thermodynamically relevant alternative conformations of the protein were identified by this procedure. One alternate conformation involved a difference in the side chain position of B/252.MET relative to the conformation of this residue in the optimal conformation, and had an energy only 0.45 kcal/mol greater than the optimal conformation. The other alternate exhibited a distinct conformation of B/313.TRP, while having an energy of only 0.61 kcal/mol greater than the optimal conformation.

CONCLUSION

The methods illustrated in FIGS. 4 and 5 may be governed by instructions that are stored in a computer readable storage medium and that are executed by at least one processor of at least one server. Each of the operations shown in FIGS. 4 and 5 may correspond to instructions stored in a non-transitory computer memory or computer readable storage medium. In various implementations, the non-transitory computer readable storage medium includes a magnetic or optical disk storage device, solid state storage devices such as Flash memory, or other non-volatile memory device or devices. The computer readable instructions stored on the non-transitory computer readable storage medium may be in source code, assembly language code, object code, or other instruction format that is interpreted and/or executable by one or more processors.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the exemplary configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method of evaluating an effect that a mutation of a polypeptide of known sequence and structure has on the polypeptide by identifying one or more conformations for the polypeptide upon incorporation of the mutation, wherein the polypeptide comprises a plurality of atoms, and wherein the polypeptide comprises at least one contiguous segment of main chain, the method comprising:

at a computer system having one or more processors and memory storing one or more programs to be executed by the one of more processors:
(A) obtaining an initial set of three-dimensional coordinates $\{x_1, \ldots, x_N\}$ for the polypeptide, wherein each respective $x_i$ in $\{x_1, \ldots, x_N\}$ is a three dimensional coordinate for an atom in the plurality of atoms in said polypeptide;
(B) identifying, in silico, a residue of the polypeptide, and replacing the residue with a different residue, thereby defining a sequence of a mutated polypeptide;
(C) identifying a region of the polypeptide based upon the identity of the replaced residue of the mutated polypeptide, the region comprising a plurality of residues;
(D) altering a side-chain rotamer conformation, with respect to the initial set of three-dimensional coordinates $\{x_1, \ldots, x_N\}$ of each residue in a subset of residues in the region of the polypeptide, for each respective subset of residues in the region of the polypeptide in a plurality of subsets of residues in the region of the polypeptide, thereby deriving a plurality of mutated polypeptide structures of the region of the polypeptide,
wherein each respective subset of residues in the plurality of subsets of residues in the region of the polypeptide is selected from among all the residues in the region of the polypeptide using a deterministic, randomized or pseudo-randomized algorithm;
(E) generating a plurality of sets of clusters for each respective residue in the region of the polypeptide, using the plurality of mutated polypeptide structures derived in (D), wherein
each respective set of clusters in the plurality of sets of clusters is for
(i) a side chain or a main chain of a respective residue in the region of the polypeptide in which each respective cluster in the respective set of clusters is formed by clustering a conformation of the side chain or main chain of the respective residue in each mutated polypeptide structure in the plurality of mutated polypeptide structures derived in (D) or
(ii) a contiguous segment of the main chain in the at least one contiguous segment of main chain in the region of the polypeptide in which each respective cluster in the respective set of clusters is formed by clustering a structural metric associated with the main chain of the contiguous segment of the main chain in each mutated polypeptide structure in the plurality of mutated polypeptide structures derived in (D);
(F) grouping respective mutated polypeptide structures in the plurality of mutated polypeptide structures into a plurality of subgroups, wherein each mutated polypeptide structure in a subgroup in the plurality of subgroups falls into the same cluster in a threshold number of the sets of clusters in the plurality of sets of clusters; and
(G) determining a free energy estimate or configurational entropy of a plurality of mutated polypeptide structures in each subgroup in the plurality of subgroups, thereby identifying the effect that the mutation of the polypeptide has on the polypeptide in the form of the free energy estimate or the configurational entropy in each subgroup in the plurality of subgroups.

2. The method of claim 1, wherein two residues of the polypeptide are replaced in the identifying (B) with different residues.

3. The method of claim 1, wherein the region of the polypeptide consists of the atoms in the plurality of atoms that are within a distance threshold of an atom of the residue identified in (B).

4. The method of claim 1, wherein the region of the polypeptide consists of the atoms in the plurality of atoms that are within a distance threshold of a point proximate to the residue identified in (B).

5. The method of claim 4 wherein the distance threshold is 15 Angstroms.

6. The method of claim 1 wherein the identifying (B) comprises identifying a contiguous set of residues and wherein a coordinate of one or more main chain atoms in each residue in the contiguous set of residues is altered.

7. The method of claim 1 wherein the identifying (B) comprises identifying a non-contiguous set of residues and wherein a coordinate of one or more main chain atoms in each residue in the non-contiguous set of residues is altered.

8. The method of claim 1 wherein the altering of the conformation, for each respective subset of residues in the region of the polypeptide in the plurality of subsets of residues in the region of the polypeptide comprises:
(i) setting a value t and defining an initial structure to be the initial set of three-dimensional coordinates $\{x_1, \ldots, x_N\}$ for the polypeptide;
(ii) altering a conformation of each residue in a subset of residues in the polypeptide from that found in the initial structure thereby deriving a structure in the plurality of structures;
(iii) accepting the structure derived in (ii) as the initial structure when an energetic score of the structure derived in (ii) is less than an energetic score of the initial structure;
(iv) accepting, with a probability $P(\Delta E)$, the structure derived in (ii) as the initial structure when the energetic score of the structure derived in (ii) is greater than the energetic score of the initial structure, wherein $P(\Delta E)$ is a probability function that is dependent upon (1) a difference in the energetic score between the initial structure and the structure derived in (ii) and (2) the value t;
(v) decreasing the value t by an amount; and
(vi) executing (ii) through (v) until a first occurrence of an exit condition, thereby deriving the plurality of structures of the region of the polypeptide.

9. The method of claim 8, wherein $P(\Delta E) = \exp^{-[(\Delta E)/(k*t)]}$, and wherein $\Delta E$ is a difference in score between the initial structure and the structure derived in (ii) and k is a constant.

10. The method of claim 1, wherein the plurality of structures of the region of the polypeptide derived by the altering D are found using a genetic algorithm.

11. The method of claim 1, wherein the polypeptide is a protein and the altering (D) alters a side chain of a residue in a subset of residues in the region of the polypeptide to a rotamer for the side chain found in a rotamer library.

12. The method of claim 11, wherein the rotamer for the side chain found in the rotamer library is selected from the rotamer library on a deterministic, random or pseudo-random basis.

13. The method of claim 1, wherein the polypeptide is a protein and the altering (D) alters a side chain of a residue in a subset of residues in the region of the polypeptide to a conformation selected from a continuum of conformations for the side chain.

14. The method of claim 13, wherein the conformation is selected from the continuum of conformations for the side chain on a deterministic, random or pseudo-random basis.

15. The method of claim 1, wherein the generating (E) generates a set of clusters in the plurality of sets of clusters for a residue in the polypeptide using a clustering algorithm.

16. The method of claim 15, wherein the clustering algorithm comprises hierarchical clustering.

17. The method of claim 16, wherein the clustering algorithm comprises maximal linkage agglomerative clustering.

18. The method of claim 16, wherein the clustering algorithm comprises agglomerative clustering using (i) a nearest neighbor algorithm, (ii) a farthest-neighbor algorithm, (iii) an average linkage algorithm, (iv) a centroid algorithm, or (v) a sum-of-squares algorithm.

19. The method of claim 15, wherein the clustering algorithm comprises k-means clustering, fuzzy k-means clustering, Jarvis-Patrick or steepest-descent clustering.

20. The method of claim 1, wherein the threshold number of the sets of clusters is all the sets of clusters in the plurality of sets of clusters.

21. The method of claim 1, wherein the threshold number of the sets of clusters is all but one of the sets of clusters in the plurality of sets of clusters.

22. The method of claim 1, wherein the threshold number of the sets of clusters is ninety percent of the sets of clusters in the plurality of sets of clusters.

23. The method of claim 1, wherein sets of clusters in the plurality of clusters are selected on the basis of a physical property of the polypeptide.

24. The method of claim 1, the method further comprising:
(H) displaying a representation of the structures in each subgroup in the plurality of subgroups;
(I) receiving a selection of a subgroup in the plurality of subgroups;
(J) using a representation of the structures of the subgroup selected in (I) as an initial set of three-dimensional coordinates $\{x_1, \ldots, x_N\}$ for the polypeptide; and
(K) repeating (D) through (G).

25. The method of claim 1, the method further comprising:
(H) displaying a representation of the structures in each subgroup in the plurality of subgroups;
(I) receiving a selection of a subgroup in the plurality of subgroups;
(J) using a representation of the structures of the subgroup selected in (I) as an initial set of three-dimensional coordinates $\{x_1, \ldots, x_N\}$ for the polypeptide; and
(K) repeating (B) through (G).

26. The method of claim 1, wherein the initial set of three-dimensional coordinates $\{x_1, \ldots, x_N\}$ for the polypeptide are obtained by x-ray crystallography, nuclear magnetic resonance, electron microscopy, or computer modeling.

27. The method of claim 1, wherein the region of the polypeptide comprises ten residues.

28. The method of claim 1, wherein the region of the polypeptide comprises one hundred residues.

29. A computer system for evaluating an effect that a mutation of a polypeptide of known sequence and structure has on the polypeptide by identifying one or more conformations for the polypeptide upon incorporation of the mutation, wherein the polypeptide comprises a plurality of atoms, and wherein the polypeptide comprises at least one contiguous segment of main chain, the computer system comprising at least one processor and memory storing at least one program for execution by the at least one processor, the memory further comprising instructions for:

(A) obtaining an initial set of three-dimensional coordinates $\{x_1, \ldots, x_N\}$ for the polypeptide, wherein each respective $x_1$ in $\{x_1, \ldots, x_N\}$ is a three dimensional coordinate atom in the plurality of atoms in said polypeptide;
(B) identifying, in silico, a residue of the polypeptide, and replacing the residue with a different residue, thereby defining a sequence of a mutated polypeptide;
(C) identifying a region of the polypeptide based upon the identity of the replaced residue of the mutated polypeptide, the region comprising a plurality of residues;
(D) altering a side-chain rotatmer conformation, with respect to the initial set of three-dimensional coordinates $\{x_1, \ldots, x_N\}$ of each residue in a subset of residues in the region of the polypeptide, for each respective subset of residues in the region of the polypeptide in a plurality of subsets of residues in the region of the polypeptide, thereby deriving a plurality of mutated polypeptide structures of the region of the polypeptide,
wherein each respective subset of residues in the plurality of subsets of residues in the region of the polypeptide is selected from among all the residues in the region of the polypeptide using a deterministic, randomized or pseudo-randomized algorithm;
(E) generating a plurality of sets of clusters for each respective residue in the region of the polypeptide using the plurality of mutated polypeptide structures derived in (D), wherein
each respective set of clusters in the plurality of sets of clusters is for
(i) a side chain or a main chain of a respective residue in the region of the polypeptide in which each respective cluster in the respective set of clusters is formed by clustering a conformation of the side chain or main chain of the respective residue in each mutated polypeptide structure in the plurality of mutated polypeptide structures derived in (D) or
(ii) a contiguous segment of the main chain in the at least one contiguous segment of main chain in the region of the polypeptide in which each respective cluster in the respective set of clusters is formed by clustering a structural metric associated with the main chain of the contiguous segment of the main chain in each mutated polypeptide structure in the plurality of mutated polypeptide structures derived in (D),
(F) grouping respective mutated polypeptide structures in the plurality of mutated polypeptide structures into a plurality of subgroups, wherein each mutated polypeptide structure in a subgroup in the plurality of subgroups falls into the same cluster in a threshold number of the sets of clusters in the plurality of sets of clusters; and
(G) determining a free energy estimate or configurational entropy of a plurality of mutated polypeptide structures in each subgroup in the plurality of subgroups, thereby identifying the effect that the mutation of the polypeptide has on the polypeptide in the form of the free energy estimate or the configurational entropy in each subgroup in the plurality of subgroups.

30. A non-transitory computer readable storage medium storing a computational module for evaluating an effect that a mutation of a polypeptide of known sequence and structure has on the polypeptide by identifying one or more conformations for the polypeptide upon incorporation of the mutation, wherein the polypeptide comprises a plurality of atoms, and wherein the polypeptide comprises at least one contiguous segment of main chain, the computational module comprising instructions for:

(A) obtaining an initial set of three-dimensional coordinates $\{x_1, \ldots, x_N\}$ for the polypeptide, wherein each respective $x_i$ in $\{x_1, \ldots, x_N\}$ is a three dimensional coordinate for an atom in the plurality of atoms in said polypeptide;

(B) identifying, in silico, a residue of the polypeptide, and replacing the residue with a different residue, thereby defining a sequence of the mutated polypeptide;

(C) identifying a region of the polypeptide based upon the identity of the replaced residue of the mutated polypeptide, the region comprising a plurality of residues;

(D) altering a side-chain rotamer conformation, with respect to the initial set of three-dimensional coordinates $\{x_1, x_N\}$ of each residue in a subset of residues in the region of the polypeptide, for each respective subset of residues in the region of the polypeptide in a plurality of subsets of residues in the region of the polypeptide, thereby deriving a plurality of mutated polypeptide structures of the region of the polypeptide, wherein each respective subset of residues in the plurality of subsets of residues in the region of the polypeptide is selected from among all the residues in the region of the polypeptide using a deterministic, randomized or pseudo-randomized algorithm;

(E) generating a plurality of sets of clusters for each respective in the region of the polypeptide, using the plurality of mutated polypeptide structures derived in (D), wherein each respective set of clusters in the plurality of sets of clusters is for (i) a side chain or a main chain of a respective residue in the region of the polypeptide in which each respective cluster in the respective set of clusters is formed by clustering a conformation of the side chain or main chain of the respective residue in each mutated polypeptide structure in the plurality of mutated polypeptide structures derived in (D) or (ii) a contiguous segment of the main chain in the at least one contiguous segment of main chain in the region of the polypeptide in which each respective cluster in the respective set of clusters is formed by clustering a structural metric associated with the main chain of the contiguous segment of the main chain in each mutated polypeptide structure in the plurality of mutated polypeptide structures derived in (D);

(F) grouping respective mutated polypeptide structures in the plurality of mutated polypeptide structures into a plurality of subgroups, wherein each mutated polypeptide structure in a subgroup in the plurality of subgroups falls into the same cluster in a threshold number of the sets of clusters in the plurality of sets of clusters; and (G) determining a free energy estimate or configurational entropy of a plurality of mutated polypeptide structures in each subgroup in the plurality of subgroups, thereby identifying the effect that the mutation of the polypeptide has on the polypeptide in the form of the free energy estimate or the configurational entropy in each subgroup in the plurality of subgroups.

\* \* \* \* \*